(12) United States Patent
Wooder et al.

(10) Patent No.: US 12,203,848 B2
(45) Date of Patent: Jan. 21, 2025

(54) APPARATUS, SYSTEM AND METHOD FOR MEASURING PROPERTIES OF A SAMPLE

(71) Applicant: ODx Innovations Limited, Inverness (GB)

(72) Inventors: Nicholas Wooder, Melbourn (GB); Alexander Carr, Melbourn (GB); Piers Harding, Melbourn (GB); Giles Sanders, Melbourn (GB); Ewan Chirnside, Inverness (GB); Mike Malecha, Inverness (GB)

(73) Assignee: ODX INNOVATIONS LIMITED, Hercules, CA (US)

( * ) Notice: Subject to any disclaimer, the term of this patent is extended or adjusted under 35 U.S.C. 154(b) by 144 days.

(21) Appl. No.: 17/796,581

(22) PCT Filed: Feb. 1, 2021

(86) PCT No.: PCT/GB2021/050223
§ 371 (c)(1),
(2) Date: Jul. 29, 2022

(87) PCT Pub. No.: WO2021/152335
PCT Pub. Date: Aug. 5, 2021

(65) Prior Publication Data
US 2023/0052166 A1 Feb. 16, 2023

(30) Foreign Application Priority Data

Jan. 31, 2020 (GB) ..................... 2001397

(51) Int. Cl.
*G01N 21/51* (2006.01)
*G01N 21/47* (2006.01)

(52) U.S. Cl.
CPC ..... *G01N 21/51* (2013.01); *G01N 2021/4707* (2013.01); *G01N 2021/4711* (2013.01)

(58) Field of Classification Search
CPC .. G01N 15/1459; G01N 33/493; G01N 21/51; G01N 2015/1006;
(Continued)

(56) References Cited

U.S. PATENT DOCUMENTS 2,707,900 A 5/1955 Maresh et al.
3,562,524 A 2/1971 Moore et al.
(Continued)

FOREIGN PATENT DOCUMENTS

CN 2663979 Y 12/2004
CN 101218507 A 7/2008
(Continued)

OTHER PUBLICATIONS

International Search Report for International Patent Application No. PCT/GB2021/050223; European Patent Office; Rijswijk, Netherlands; date of mailing May 25, 2021.
(Continued)

*Primary Examiner* — Michael P Stafira
(74) *Attorney, Agent, or Firm* — Thomas E. Lees, LLC

(57) ABSTRACT

A device (1) comprising an optical apparatus (2) for monitoring bacterial growth of a drug-dosed liquid biological sample. A sample container port for receiving a sample container (6), in use, is provided in the device, the sample container (6) having at least one detection chamber (20) for containing the drug-dosed sample. The optical apparatus (2) comprises a light source (22) configured to emit light along an incident beam axis that, in use, intersects with at least one detection chamber (20) of the sample container (6), and to illuminate the drug-dosed sample contained within the detection chamber (20). The optical apparatus (20) comprises a first photodetector (26) configured to receive light scattered by bacteria in the sample. The optical apparatus (2) comprises a light collection arrangement (24) configured to
(Continued)

collect light exiting the detection chamber (20) that has been scattered in a forward direction by bacteria in the sample, in a range of scattering angles between about +/−4 and +/−20 degrees relative to the incident beam axis, and to direct the collected scattered light to the first photodetector (26); and prevent non-scattered light travelling parallel to the incident beam axis and exiting the detection chamber (20) from reaching the first photodetector (26). The optical apparatus (2) comprises at least one processor configured to: measure an intensity of the scattered light received by the first photodetector (26); determine a corresponding representative amount or concentration of bacteria present in the sample based on the intensity of the scattered light; repeat the measuring and determining steps at a series of predetermined intervals to determine changes in the representative amount or concentration of bacteria present in the sample as a function of time; and determine a corresponding susceptibility of the bacteria in the sample to the respective drug.

22 Claims, 14 Drawing Sheets

(58) Field of Classification Search
CPC ....... G01N 2015/1402; G01N 15/1434; G01N 15/14; G01N 2021/4707; G01N 15/1429; G01N 33/56911; G01N 15/1404; G01N 2015/1486; G01N 21/6486; G01N 2021/513; G01N 15/01; G01N 33/582; G01N 2015/016; G01N 2021/6439; G01N 1/30; G01N 2015/1493; G01N 2015/1477; G01N 1/38; G01N 15/147; G01N 21/53; G01N 21/6428; G01N 33/5094; G01N 21/645; G01N 33/487; G01N 35/00; G01N 15/1425; G01N 33/569; G01N 21/49; G01N 21/0303; G01N 33/68; G01N 15/075; G01N 33/4833; G01N 15/0211; G01N 15/1012; G01N 2015/1497; G01N 1/10; G01N 33/5005; G01N 21/05; G01N 2201/06113; G01N 1/20; G01N 1/31; G01N 15/1456; G01N 2001/031; G01N 2015/011; G01N 21/47; G01N 21/76; G01N 2201/0415; G01N 15/06; G01N 15/1484; G01N 33/56961; G01N 15/1436; G01N 15/149; G01N 21/64; G01N 33/52; G01N 15/1433; G01N 2021/4709; G01N 2021/4711; G01N 2015/012; G01N 2201/0612; G01N 2201/065; G01N 15/0205; G01N 2015/019; G01N 2015/1413; G01N 33/80; G01N 2015/018; G01N 21/031; G01N 2333/22; G01N 2500/02; G01N 2015/0222; G01N 21/11; G01N 21/21; G01N 2800/52; G01N 33/5041; G01N 21/78; G01N 2201/061; G01N 2333/40; G01N 35/00871; G01N 35/1004; G01N 1/14; G01N 15/1409; G01N 2001/302; G01N 2021/6482; G01N 2201/0231; G01N 2800/062; G01N 33/6893; G01N 35/00732; G01N 35/04; G01N 2015/1488; G01N 2035/00881; G01N 33/56916; G01N 33/573; G01N 33/588; G01N 35/1095; G01N 2015/0053; G01N 2015/1411; G01N 2015/1452; G01N 2021/4726; G01N 2021/6469; G01N 2035/00851; G01N 21/1717; G01N 21/255; G01N 21/474; G01N 2201/0642; G01N 33/5091; G01N 35/026; G01N 15/1427; G01N 2015/1028; G01N 2015/142; G01N 2015/144; G01N 33/56966; G01N 33/57434; G01N 33/6854; G01N 1/405; G01N 15/1023; G01N 2001/028; G01N 2021/0357; G01N 2035/00277; G01N 21/0332; G01N 2201/068; G01N 2201/127; G01N 2333/245; G01N 2333/39; G01N 2469/20; G01N 2500/10; G01N 33/483; G01N 33/48792; G01N 33/56938; G01N 33/56944; G01N 33/689; G01N 15/05; G01N 2015/0046; G01N 2015/1014; G01N 21/4788; G01N 21/532; G01N 2333/916; G01N 2800/26; G01N 33/57438; G01N 33/57488; G01N 1/4077; G01N 15/0631; G01N 2015/035; G01N 2021/0346; G01N 2021/7759; G01N 2035/00326; G01N 2035/00831; G01N 2035/0465; G01N 2035/0491; G01N 21/55; G01N 21/6402; G01N 21/6452; G01N 2201/0245; G01N 2201/025; G01N 2201/125; G01N 2201/1296; G01N 2333/195; G01N 2333/914; G01N 2333/924; G01N 2500/04; G01N 2800/348; G01N 33/04; G01N 33/1893; G01N 33/49; G01N 33/505; G01N 33/574; G01N 33/86; G01N 35/00603; G01N 35/02; G01N 15/00; G01N 15/10; G01N 2001/4088; G01N 2015/0092; G01N 2015/03; G01N 2021/6478; G01N 2035/00891; G01N 2035/0091; G01N 2201/1045; G01N 2333/20; G01N 2333/70503; G01N 33/18; G01N 33/4915; G01N 33/564; G01N 33/56972; G01N 33/56983; G01N 35/00069; G01N 35/00722; G01N 2015/0277; G01N 2021/0382; G01N 2021/0389; G01N 2021/4704; G01N 2021/4769; G01N 2021/479; G01N 2021/6463; G01N 2035/00811; G01N 21/03; G01N 21/94; G01N 2201/04; G01N 2201/064; G01N 2333/28; G01N 2333/4712; G01N 2333/918; G01N 2333/936; G01N 2333/96419; G01N 2800/2828; G01N 2800/7028; G01N 33/4875; G01N 33/502; G01N 33/5088; G01N 33/57415; G01N 33/577; G01N 35/00594; G01N 15/0255; G01N 2015/1019; G01N 2015/1029; G01N 2015/1415; G01N 2021/6421; G01N 2021/6441; G01N 2021/6484; G01N 21/01; G01N 21/85; G01N 2333/255; G01N 2800/24; G01N 33/50; G01N 33/5008; G01N 33/5011; G01N 33/5047; G01N 33/5306; G01N 33/5375; G01N 33/54313; G01N 33/54346; G01N 33/5438; G01N 33/561; G01N 33/6866; G01N 1/2035; G01N 1/2202; G01N 1/4005; G01N 15/0625; G01N 15/1031; G01N 2001/1006; G01N 2001/1418; G01N 2001/305; G01N 2015/0294; G01N 2015/0681; G01N 2015/0687; G01N
2021/1765; G01N 2021/4735; G01N
2035/0405; G01N 21/23; G01N 21/253;
G01N 21/39; G01N 21/4785; G01N
21/59; G01N 2201/103; G01N 2333/165;
G01N 2333/31; G01N 2333/4716; G01N
2333/8135; G01N 2500/00; G01N
2800/02; G01N 2800/042; G01N
2800/065; G01N 2800/32; G01N 31/22;
G01N 33/15; G01N 33/5023; G01N
33/5058; G01N 33/5064; G01N 33/532;
G01N 33/533; G01N 33/54326; G01N
33/5436; G01N 33/554; G01N 33/56988;
G01N 33/6869; G01N 33/6872; G01N
33/6896; G01N 35/1009; G01N 1/34;
G01N 15/0227; G01N 15/12; G01N
17/006; G01N 2001/045; G01N
2001/2886; G01N 2001/4083; G01N
2015/0238; G01N 2015/025; G01N
2015/0261; G01N 2015/0288; G01N
2015/1024; G01N 2015/1447; G01N
2015/145; G01N 2021/0321; G01N
2021/4792; G01N 2035/00158; G01N
2035/00178; G01N 2035/00306; G01N
21/17; G01N 21/274; G01N 21/278;
G01N 21/3577; G01N 21/453; G01N
21/6408; G01N 21/65; G01N 21/658;
G01N 21/75; G01N 2201/1293; G01N
2333/315; G01N 2333/335; G01N
2333/43595; G01N 2333/4727; G01N
2333/5428; G01N 2333/57; G01N
2333/705; G01N 2333/70578; G01N
2333/70596; G01N 2333/72; G01N
2333/726; G01N 2333/78; G01N
2333/9108; G01N 2333/912; G01N
2333/91205; G01N 2333/96486; G01N
2400/50; G01N 2446/20; G01N 2446/40;
G01N 2446/60; G01N 2446/64; G01N
2446/66; G01N 2469/10; G01N 2510/00;
G01N 2800/28; G01N 2800/2821; G01N
2800/50; G01N 2800/7095; G01N
33/1826; G01N 33/491; G01N 33/5029;
G01N 33/5038; G01N 33/5052; G01N
33/5302; G01N 33/5308; G01N 33/5432;
G01N 33/5434; G01N 33/54353; G01N
33/54366; G01N 33/566; G01N
33/56905; G01N 33/5695; G01N
33/5748; G01N 33/57492; G01N 33/74;
G01N 33/96; G01N 35/028; G01N
35/1083; G01N 5/00

See application file for complete search history.

(56) References Cited

U.S. PATENT DOCUMENTS

| | | | |
|---|---|---|---|
| 3,772,154 A | 11/1973 | Isenberg et al. | |
| 3,826,574 A | 7/1974 | Brown, Jr. | |
| 3,837,746 A | 9/1974 | Acker et al. | |
| 3,946,239 A | 3/1976 | Salzman et al. | |
| 3,983,006 A | 9/1976 | Acker et al. | |
| 4,013,368 A | 3/1977 | Acker et al. | |
| 4,076,420 A | 2/1978 | DeMaeyer et al. | |
| 4,416,995 A | 11/1983 | Amaral | |
| 4,690,560 A | 9/1987 | Coogan | |
| 4,942,305 A | 7/1990 | Sommer | |
| 5,043,591 A | 8/1991 | Ludlow et al. | |
| 5,164,597 A | 11/1992 | Lodder | |
| 5,164,796 A | 11/1992 | DiGuiseppi et al. | |
| 5,525,475 A | 6/1996 | Ladouceur | |
| 5,701,012 A * | 12/1997 | Ho | G01N 15/1459 250/461.2 |
| 6,618,144 B1 | 9/2003 | Reed | |
| 7,173,697 B1 | 2/2007 | Moosmuller et al. | |
| 7,209,231 B2 * | 4/2007 | Rastopov | G01N 15/0211 356/339 |
| 9,116,121 B2 | 8/2015 | Kaye et al. | |
| 9,677,988 B1 | 6/2017 | Doggett | |
| 10,029,249 B1 | 7/2018 | Vittur et al. | |
| 10,670,521 B2 | 6/2020 | Hammond et al. | |
| 10,677,727 B2 | 6/2020 | Hammond et al. | |
| 11,609,178 B2 | 3/2023 | Gillespie | |
| 2002/0033939 A1 | 3/2002 | Hansen | |
| 2002/0197740 A1 | 12/2002 | Hansen et al. | |
| 2003/0111607 A1 | 6/2003 | Bachur, Jr. et al. | |
| 2003/0153021 A1 | 8/2003 | Lu et al. | |
| 2004/0191125 A1 | 9/2004 | Kellogg et al. | |
| 2006/0043298 A1 | 3/2006 | Kawase et al. | |
| 2007/0086916 A1 | 4/2007 | LeBoeuf et al. | |
| 2007/0146841 A1 | 6/2007 | Moosmuller et al. | |
| 2008/0221711 A1 | 9/2008 | Trainer | |
| 2010/0020323 A1 | 1/2010 | Moosmuller et al. | |
| 2010/0273208 A1 | 10/2010 | Takenaka et al. | |
| 2011/0066382 A1 * | 3/2011 | Adams | G01N 33/1893 702/19 |
| 2012/0003661 A1 | 1/2012 | Eckert et al. | |
| 2014/0240695 A1 | 8/2014 | Pagan et al. | |
| 2014/0356129 A1 | 12/2014 | Paust et al. | |
| 2014/0377795 A1 | 12/2014 | Gannot et al. | |
| 2015/0040689 A1 | 2/2015 | Jayne et al. | |
| 2015/0098086 A1 * | 4/2015 | Moitzi | G01N 21/47 356/446 |
| 2015/0107993 A1 | 4/2015 | Izquierdo et al. | |
| 2015/0160119 A1 | 6/2015 | Marshall et al. | |
| 2016/0161404 A1 | 6/2016 | Marshall et al. | |
| 2016/0216204 A1 | 7/2016 | Marshall et al. | |
| 2016/0313233 A1 | 10/2016 | Zangmeister et al. | |
| 2016/0349178 A1 | 12/2016 | Walsh et al. | |
| 2018/0031472 A1 | 2/2018 | Hammond et al. | |
| 2018/0313753 A1 | 11/2018 | Marshall et al. | |
| 2020/0249148 A1 * | 8/2020 | Tomaras | G01N 15/06 |
| 2023/0061115 A1 | 3/2023 | Murray et al. | |

FOREIGN PATENT DOCUMENTS

| | | | |
|---|---|---|---|
| CN | 201277944 Y | 7/2009 | |
| CN | 105115902 A | 12/2015 | |
| CN | 105190291 A | 12/2015 | |
| CN | 105308434 A | 2/2016 | |
| CN | 105339777 A | 2/2016 | |
| CN | 107003230 A | 8/2017 | |
| EP | 0781990 A1 | 7/1997 | |
| EP | 2124028 A1 | 11/2009 | |
| EP | 2261641 A2 | 12/2010 | |
| EP | 2320212 A1 | 5/2011 | |
| EP | 2869055 A1 * | 5/2015 | G01N 15/0205 |
| EP | 2869057 A1 * | 5/2015 | G01N 15/0205 |
| GB | 2369182 A * | 5/2002 | G01N 15/0211 |
| GB | 2432660 A * | 5/2007 | B01L 3/50 |
| GB | 2434444 A | 7/2007 | |
| GB | 2496690 A | 5/2013 | |
| GB | 2550602 A | 11/2017 | |
| JP | S49114493 A | 10/1974 | |
| JP | S5062481 A | 5/1975 | |
| JP | 61195685 A | 8/1986 | |
| JP | S61195685 A | 8/1986 | |
| JP | 05113386 A | 5/1993 | |
| JP | 08145879 A | 6/1996 | |
| JP | 11248721 A | 9/1999 | |
| JP | 3304395 B2 | 7/2002 | |
| JP | 2002522789 A | 7/2002 | |
| JP | 2011196735 A | 10/2011 | |
| JP | 2014021112 A | 2/2014 | |
| WO | 8500426 A1 | 1/1985 | |
| WO | 9853311 A2 | 11/1998 | |
| WO | 0010010 A2 | 2/2000 | |

(56) References Cited

FOREIGN PATENT DOCUMENTS

| WO | 03064991 A2 | 8/2003 | |
|---|---|---|---|
| WO | 2005100955 A1 | 10/2005 | |
| WO | 2006018839 A2 | 2/2006 | |
| WO | 2009050536 A1 | 4/2009 | |
| WO | 2010097685 A2 | 9/2010 | |
| WO | 2014080322 A1 | 5/2014 | |
| WO | WO-2015067930 A1 * | 5/2015 | ......... G01N 15/0205 |
| WO | WO-2016006362 A1 * | 1/2016 | ............ G01N 21/03 |
| WO | 2016051267 A2 | 4/2016 | |
| WO | 2016120779 A1 | 8/2016 | |
| WO | 2016128747 A1 | 8/2016 | |
| WO | WO-2017112957 A1 * | 6/2017 | ........... A61B 5/6898 |

OTHER PUBLICATIONS

Written Opinion of the International Searching Authority for International Patent Application No. PCT/GB2021/050223; European Patent Office; Rijswijk, Netherlands; date of mailing May 25, 2021.
"Building Scientific Apparatus" 4th Edition, Cambridge University Press (Moore et al.) published 2009.

* cited by examiner

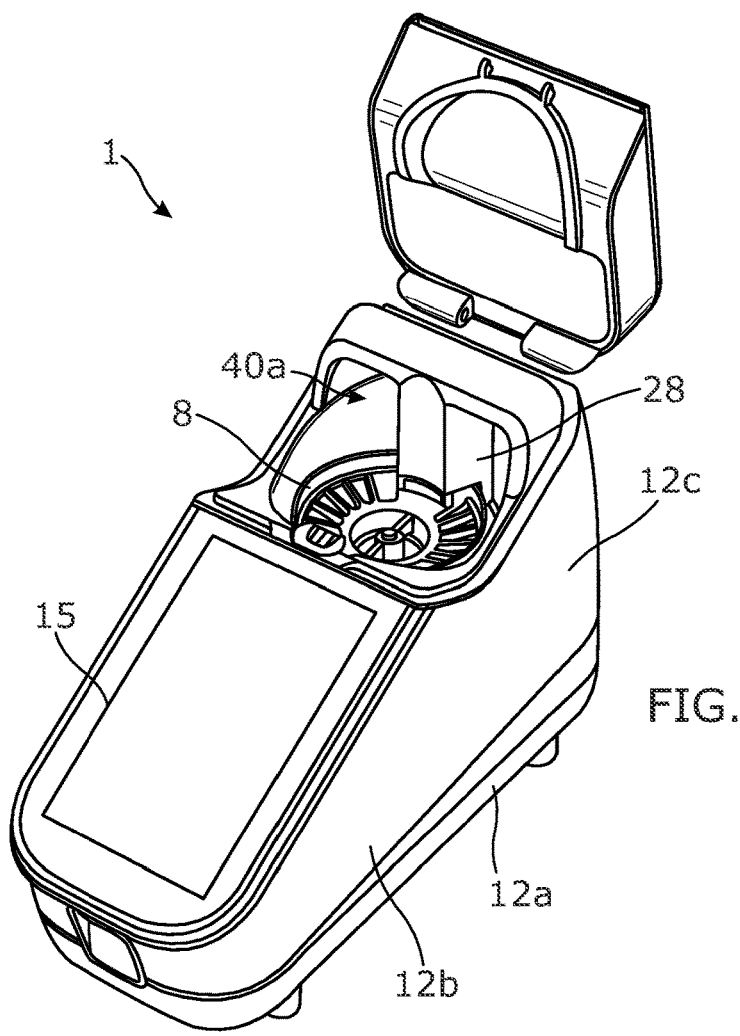
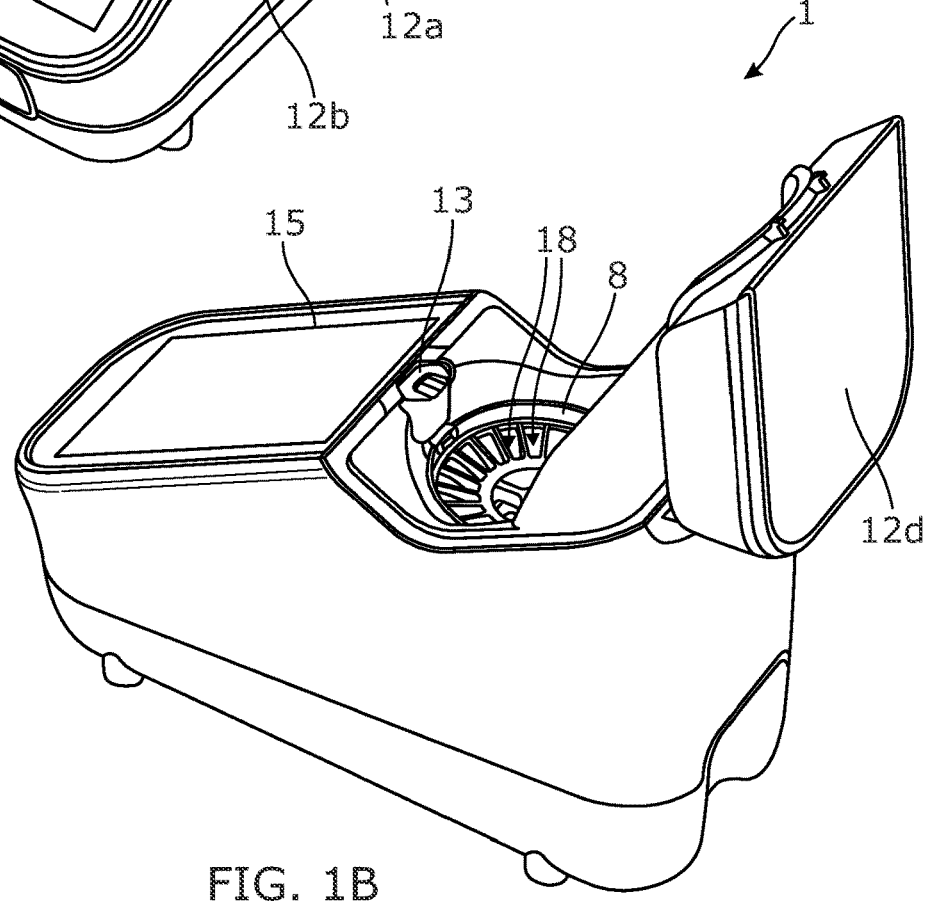
FIG. 1A
FIG. 1B

APPARATUS, SYSTEM AND METHOD FOR MEASURING PROPERTIES OF A SAMPLE

CROSS-REFERENCE TO RELATED APPLICATIONS

This application is a national stage entry under 35 USC § 371(b) of PCT International Application No. PCT/GB2021/050223, filed Feb. 1, 2021, and claims the benefit of British Patent Application No. 2001397.5, filed Jan. 31, 2020, which are expressly incorporated by reference herein.

TECHNICAL FIELD

The present disclosure relates to devices, apparatus, systems and methods for measuring properties of a sample, and in particular for measuring optical properties of a biological sample containing microorganism particles such as bacteria.

BACKGROUND

Many techniques for measuring properties of samples, and particularly for measuring optical properties of a biological sample, such as the concentration of particles within the sample, are known. For example, absorption spectrophotometers measure the relative absorbance of a sample; scattering spectrophotometers, flow cytometers and nephelometers measure light scattered by the particles in the sample.

A practical application of such measurement techniques lies in the processing and analysis of clinical samples (such as urine, blood etc.), in situations where the amount and/or type of bacteria present in a given sample is to be determined in order to ascertain the most appropriate mode of treatment (e.g., the type and dosage of an antibiotic that should be administered) for the patient/subject. For example, measuring the time-dependent bacterial concentration of a clinical sample, that has been dosed with a particular drug or antibiotic, allows bacterial susceptibility to that drug (and hence the efficacy of that drug in relation to the particular bacterial strain present in the sample) to be determined.

Various systems utilising such techniques are known to be used for these practical applications. For example, WO 2016/128747 incorporates the use of an integrating sphere light collector in which a (drug-dosed) clinical sample to be analysed is placed. When the sample is illuminated, bacteria present in the sample scatter some light; this scattered light is reflected and diffused by the reflective inner surface of the integrating sphere. WO 2019/166799 describes a similar system which comprises a pair of optically linked chambers that use an integrating light collection mechanism to detect the light scattered by the sample. WO 2018/091922 describes a combined cartridge in which a clinical sample may be initially incubated to increase the bacterial concentration present in the sample; separate portions of the sample are then subsequently combined with various different drugs/antibiotics and the optical properties of each individual sample portion are measured to determine bacterial susceptibility to each drug.

It is against this background that the present devices/apparatus, systems and methods have been devised.

BRIEF SUMMARY

According to an aspect of the disclosure, there is provided an optical apparatus/device for monitoring bacterial growth and/or determining bacterial amount or concentration in a drug-dosed liquid biological sample, the apparatus/device comprising: a light source configured to emit light along an incident beam axis that, in use, intersects with a detection chamber of a sample container containing the drug-dosed sample, and to illuminate the drug-dosed sample contained within the detection chamber; a first photodetector configured to receive light scattered by particles in the sample; a light collection arrangement configured to: collect light exiting the detection chamber that has been scattered in a forward direction by the particles in the sample, in a range of scattering angles between about +/−4 and +/−20 degrees relative to the incident beam axis, and to direct the collected scattered light to the first photodetector; and to prevent non-scattered light travelling parallel to the incident beam axis and exiting the detection chamber from reaching the first photodetector; and at least one processor configured to: measure an intensity of the scattered light received by the first photodetector; determine a corresponding representative amount or concentration of particles present in the sample based on the intensity of the scattered light; repeat the measuring and determining steps at a series of predetermined intervals to determine changes in the representative amount or concentration of particles present in the sample as a function of time; and determine a corresponding change in the amount or concentration of particles in the sample. Preferably, the particles in the sample are bacteria, and the change in representative amount or concentration of the particles as a function of time indicates the susceptibility of the bacteria in the sample to a drug/antibiotic. In some embodiments, forward-scattered light may be measured in a range of scattering angles between about +/−5 and +/−20 degrees relative to the incident beam axis.

Beneficially, the device of the present disclosure is able to capture the majority (e.g. around 95%) of forward-scattered light generated by interaction of the incident light beam with the particles in the sample, since this light is primarily scattered over relatively small scattering angles such as those set out above. The device of the present disclosure therefore maximises the amount of scattered light intensity that can be collected from a single sample, which in turns means that a relatively small sample volume may be used to nevertheless obtain statistically significant results, particularly in relation to changes in the scattered light intensity over time.

In embodiments of this aspect of the disclosure, the amount or concentration of particles/bacteria is determined quantitatively. In other embodiments it is suitable that the amount or concentration of particles/bacteria is determined qualitatively, i.e. such that a relative amount or concentration is determined as a function of time: such qualitative measurements are suitable and may be preferred for simplicity of data processing, since changes in particle/bacterial amount or concentration can generally be reliably assessed relatively to other time points and assays. In any of the embodiments of this aspect of the disclosure, the optical apparatus is configured to receive a sample container containing at least one detection chamber for containing a biological sample. The biological sample may potentially contain a pathogenic bacteria.

In some embodiments, the first photodetector may also be used in combination with a lock-in amplifier to isolate a received signal having a particular frequency. The frequency to be isolated may correspond to a modulation frequency of the light emitted from the light source. This beneficially allows noise signals from other frequencies to be filtered out, which thereby improves the signal-to-noise ratio of the obtained signal.

Suitably, the light collection arrangement is configured such that only forward scattered light in the range of angles between about +/−4 and +/−20 degrees relative to the incident beam axis is collected and directed towards the first photodetector. More particularly, the range of scattering angles of collected scattered light is between +4 and +16 degrees and −4 and −16 degrees relative to the incident beam axis, and even more particularly between +5 and +16 degrees and −5 and −16 degrees relative to the incident beam axis. Beneficially, given that the majority (around 95%) of the light scattered via interaction with particles in the sample is scattered only over a small range of angles relative to the incident light beam axis, the above-described configuration maximises the proportion of scattered light that can be collected by the first photodetector, whilst minimising the amount of non-scattered light that is also collected.

In some embodiments, the light collection arrangement comprises: (i) a concave elliptical reflector configured to collect and reflect only light in the angular range between about +/−4 and +/−20 degrees relative to the incident beam axis towards the first photodetector so that it is received by the first photodetector; or (ii) a concave elliptical reflector configured to collect and reflect forward-scattered light in the angular range between about +/−4 and +/−20 degrees relative to the incident beam axis towards a condenser, the condenser arranged to receive light reflected by the concave elliptical reflector and to focus the received light onto the first photodetector. Such a configuration advantageously allows light in the desired range of scattering angles to be collected using only one main component (or even two cooperating components), minimising the number of components that need to be included in the light collection arrangement, and which therefore need to be accurately positioned and aligned with one another. Furthermore, use of a single (appropriately shaped and sized) reflector is beneficial as it reduces the space that is required to house the light collection arrangement, which in turn may allow reduction of the size of the overall device itself. It is also noted that use of a concentrating element or condenser further increases the amount and proportion of scattered light that can be collected by the photodetector, potentially improving the sensitivity of the overall device to detect smaller changes in scattered signal intensity.

In some embodiments, wherein the light collection arrangement comprises a concave elliptical reflector shaped to reflect the forward-scattered light from the sample to the first photodetector or condenser, and wherein the concave elliptical reflector comprises an aperture aligned with the incident beam axis and configured to allow non-scattered light from the detection chamber to pass through the concave elliptical reflector. This configuration beneficially prevents non-scattered light from being inadvertently collected along with the scattered light, and helps to ensure that a representative measurement of the actual scatter (and hence a more accurate, representative determination of the amount of particles present in the sample) is obtained.

This arrangement, particularly in combination with the ranges of scattering angles described above, enables a balance to be struck between capturing as much scattered light as possible, and minimising the amount of non-scattered light that is also captured, whilst maintaining an adequate width of light source beam to illuminate the sample sufficiently and generate a significant amount of scatter. Moreover, the ability to maintain consistent alignment of the light source beam with the aperture is advantageous for optimal light collection. The non-scattered light may be directed towards a beam dump or an exit port.

In some embodiments, the optical apparatus further comprises a second photodetector arranged to receive non-scattered light; optionally wherein the second photodetector is positioned on the opposite side of the light collection arrangement to the sample, and aligned with the incident beam axis to receive the non-scattered light. Beneficially, the second photodetector enables the non-scattered ('baseline level') light to be collected and processed which, in turn, allows properties of this light to be determined. These properties may be utilised during processing of the scattered light collected by the first photodetector to implement noise reduction techniques, in the event that the noise obtained in the scattered and non-scattered light is common or correlated (e.g. noise generated as a result of vibrations from operation of a motor within the device). Additionally or alternatively the non-scattered light can be analysed to assess light source stability and to identify variations in intensity of the incident light which may affect the scattered light signal.

In some embodiments, the light collection arrangement comprises first and second condensing lenses and a mirror, wherein: the first condensing lens is configured to direct the scattered light to the second condensing lens, and to focus non-scattered light travelling along the incident beam axis onto the mirror; and the second condensing lens is configured to receive the scattered light from the first condensing lens and to focus the scattered light onto the first photodetector. The mirror may be arranged along the incident beam axis between the first and second condensing lenses and may be configured to reflect the non-scattered light away from the first photodetector. This arrangement provides an alternative configuration that enables separation of scattered and non-scattered light for respective processing and analysis, and which may provide benefits relative to the previously described light collection arrangements comprising an elliptical reflector. For example, although more components are used in the two-condensing-lens arrangement, such components may be simpler to manufacture or source (e.g. may be easier to obtain as COTS or Commercial Off-the-Shelf components).

In some embodiments, the mirror is arranged to reflect the non-scattered light towards a second photodetector, the second photodetector configured to receive the non-scattered light from the mirror. As described in relation to the configurations comprising an elliptical reflector, being able to collect and process the non-scattered light provides advantages in relation to the processing of the corresponding scattered light signal, particularly regarding noise characterisation and reduction.

Suitably, the device may further comprise a sample container carousel arranged inside the sample container port for engaging a sample container and configured to bring a detection chamber containing at least a portion of the biological sample in the sample container into alignment with the incident beam axis of the light source of the optical apparatus. Beneficially, the device may be configured to engage a separate sample container containing the sample that is to be illuminated, via use of the sample container carousel which provides the interfacing and engagement functionality between the device and the sample container. This increases the ease with which one or more samples may be aligned with the optical apparatus for measurement purposes.

In some embodiments, the device further comprises a motor operably coupled to the sample container carousel and configured to rotate the carousel to periodically bring a detection chamber containing at least a portion of the biological sample into and out of alignment with the incident beam axis of the light source. Automating the alignment of a particular sample portion with the incident light beam beneficially streamlines the measurement processes, and increases the efficiency with which multiple different measurements of scattered light intensity may be obtained, as well as the repeatability of such measurements.

Suitably, for example, the sample container carousel may be configured to engage a sample container comprising a plurality of detection chambers, and the sample container carousel may be configured to rotate so as to bring each of the plurality of detection chambers of the sample container sequentially into and out of alignment with the incident beam axis of the light source. Beneficially, the above-described configuration provides an improvement in relation to parallelisation of sample processing and analysis procedure: utilising the rotatable sample container carousel in combination with the sample container comprising multiple detection chambers means that several individual sample portions may be illuminated and the scattered light intensity obtained during the course of one measurement cycle/run. This increases the number of samples that can be analysed over a given time period, which is particularly advantageous when used in the context of determining susceptibility of bacteria in the sample to one or more different drugs (and/or drug concentrations). This in turn means that determination of an appropriate drug for treatment of a particular patient/subject may be effected quickly and efficiently, which is particularly useful when implemented for a point-of-care device.

In some embodiments, the sample container carousel comprises one or more openings configured to align with the one or plurality of detection chambers of the sample container when the sample container is correctly engaged with the sample container carousel in use.

The sample container carousel as a whole provides support and movement functionality for the sample container, and the openings provided therein may beneficially ensure that only appropriate/selected portions of the sample container (those portions corresponding to the detection chamber(s) for example) are located/placed into alignment with the incident light beam and are illuminated as desired.

In some embodiments, the sample container carousel includes one or more detectable calibration features for determining the position and/or orientation of the sample container carousel relative to the incident beam axis of the light source. The above-described configuration beneficially allows a determination to be carried out as to when a given detection chamber is or will be brought into alignment with the incident light beam, thereby ensuring that the appropriate portion or 'window' of the measured signal intensity that corresponds to the signal obtained from that particular detection chamber can be extracted, processed and analysed. This advantageously reduces the impact caused by any drifts or inconsistencies in motor rotation speed (which may occur during the course of the measurement cycle) and hence improves the signal-to-noise ratio of the obtained signal.

Suitably, the device may further comprise a calibration feature reader communicating with a processor of the device, in use, for determining a time interval between detection of a calibration feature by the calibration feature reader and an associated detection chamber coming into alignment with the incident beam axis of the light source. The calibration reader may be configured to detect the presence of a calibration feature (e.g. passing through the calibration reader itself) and associate the detection of the calibration feature with the location of an associated detection chamber of the sample container.

In some embodiments, a processor of the optical apparatus: (i) communicates with the first photodetector to measure the intensity of the scattered light received by the first photodetector during a predetermined time window corresponding to the time period during which a detection chamber of the sample container is in alignment with the incident beam axis of the light source; (ii) adjusts the length of the pre-determined intervals based on the detection of the or each calibration feature. Beneficially, this provides an alternative or additional mechanism for ensuring that a good correlation between the presence of a detection chamber in the path of the incident light beam, and the extraction or processing of an appropriate portion of the obtained signal for analysis.

In some embodiments, the processor of the optical apparatus is programmed to repeat the steps of measuring an intensity of the scattered light received by the first photodetector and determining a corresponding representative amount or concentration of bacteria present in the sample as a function of time periodically over a time period of: between about 20 minutes and about 2 hours, between about 20 minutes and about 1.5 hours, between about 20 minutes and about 1 hour or between about 30 minutes and about 1 hour. The device enables the scattered light intensity to be monitored and analysed over a prolonged period of time, such that changes in the measured intensity over that time period can be detected and assessed. For example, such changes may be used to determine changes in number of particles in the sample, which indicates associated changes in bacterial growth within the sample and may indicate increased susceptibility (or lack thereof) of the bacteria to a particular drug that is being tested.

In some embodiments, the device may comprise a temperature control system for controlling the temperature of air inside the device. Suitably, the device may further comprise at least one heating element and, optionally at least one air flow regulator arranged, in use, to bring warm air into contact with a sample container received inside the sample container port of the optical apparatus, so as to maintain a biological sample within a detection chamber at a desired temperature. For example, to maintain the temperature between around 36 to 37° C., which is an advantageous temperature to maintain in relation to the growth of bacteria within the sample under analysis; maintenance of such a temperature over the course of the measurement cycle optimises conditions for bacteria growth during the measurement cycle.

In some embodiments comprising a pair of heating elements, each heating element operably associated with a fan to push warmed air towards the sample container port, in use to heat a sample within a detection chamber of a sample container received within the port of the device. Such configurations may be particularly beneficial or useful for ensuring that an even flow of heated air is passing through and over the sample container in situ within the device, to maintain a desired temperature profile across the sample container.

In some embodiments, the light source of the optical apparatus is a laser light source, for example between 620 nm and 780 nm, or in the range of wavelengths corresponding to visible red light, when utilised in relation to a sample comprising urine of a patient or subject. However, other wavelengths of light may also be utilised, particularly when the sample corresponds to other biological fluids such as blood. It is also noted that the use of a laser light source (such a laser diode) enables the frequency and amplitude of the light emitted to be relatively easily controlled and modulated as desired; the phase of the modulating signal may also be controlled.

In some embodiments, the pre-determined intervals correspond to about 0.6 seconds at a rotational speed of 100 rpm. This corresponds to an appropriate measurement frequency at a suitable motor speed, although it will be appreciated that the measurement frequency and/or motor speed can be altered as desired (for example, faster rotational speeds of around 200 rpm could also be utilised which would apply greater forces on the fluid sample in question); in addition, processing of the obtained signals may involve the averaging of multiple individual measurements, which is beneficial in relation to noise reduction.

In some embodiments, the processor of the optical apparatus is configured to identify a plurality of periodically occurring peak features in the measured light intensity, and to carry out the measuring and determining steps only between adjacent peak features. This configuration advantageously ensures that the desired portion of the signal—corresponding to the scattered light generated by interaction with a sample in a detection chamber—is extracted from the obtained signal. It also minimises the noise level within the extracted signal, for example by avoiding inclusion within the extracted signal of light scattered by other portions of the device (e.g., with portions of the sample container or sample container carousel that do not contain any sample). This improves the signal-to-noise ratio of the signal that is being processed.

According to another aspect of the disclosure, there is provided a system for monitoring bacterial growth of a drug-dosed liquid biological sample, the system comprising: the device/apparatus as defined hereinabove; and a sample container comprising a plurality of detection chambers, each detection chamber configured to contain a drug-dosed liquid biological sample; wherein the system further comprises: a sample positioning mechanism configured to align each of the plurality of detection chambers in turn with the incident beam axis such that the light source illuminates the drug-dosed liquid biological sample contained within the illuminated detection chamber. As described above in relation to the device/apparatus, the ability to simultaneously process multiple different samples in the course of one measurement cycle has benefits in relation to parallelisation of sample processing, with the corresponding increases in speed and efficiency with which useful results may be obtained, and decreases in the associated cost.

Suitably, the sample positioning mechanism may comprise a rotation or carousel mechanism configured to rotate the sample container, so as to sequentially align each of the plurality of detection chambers with the incident beam axis.

In some embodiments, the system may further comprise a support structure arranged to support the optical apparatus. The provision of such a support structure may beneficially allow the optical components to be decoupled or isolated from the rest of the system components, which for example reduces the effects of vibration that may be generated by operation of the sample positioning mechanism/motor on the optical components and their alignment with one another during measurement. The support structure may comprise an opening configured to receive a portion of the sample container comprising at least one of the plurality of detection chambers, such that when the portion of the sample container is located within the opening, at least one of the plurality of detection chambers is locatable along the incident beam axis between the light source and the light collector. This configuration beneficially ensures good/appropriate alignment of the sample container (and of each detection chamber provided therein) with the incident light beam. In addition, the provision of an appropriately configured opening in the support structure may have benefits in relation to guiding the user to correctly interface the sample container with the sample port when inserting the sample container into the device.

Suitably, the system may further comprise a temperature control system configured to maintain the temperature of the liquid biological sample at a temperature between about 35° and 37.5°. In some embodiments, the temperature control system comprises a heating arrangement comprises a heating element arranged to generate heat, and an air circulation system configured to evenly distribute the generated heat across the plurality of detection chambers of the sample container. In some embodiments, the circulation system comprises at least one recirculation duct and an associated fan arranged to drive airflow across the heating element. As described above in relation to the device, this arrangement maintains an appropriate, desired temperature within the device and around the sample container which is suitable to promote growth of bacteria within the samples. This increases the concentration of bacteria within the sample, thereby increasing the corresponding scattered light intensity that can be obtained from a given sample volume.

According to another aspect of the disclosure, there is provided a method for determining susceptibility of bacteria in a sample to a drug, the method comprising: containing a drug-dosed liquid biological sample in a detection chamber of a sample container; illuminating, by a light source, the sample in the detection chamber with light emitted along an incident beam axis that passes through the detection chamber; collecting, by a light collector, light scattered by interaction with bacteria in the sample, the light being scattered in a forward direction in a range of scattering angles between +/−4 and +/−20 degrees relative to the incident beam axis; concentrating, by the light collector, the collected scattered light onto a first photodetector; determining, by a processor an intensity of scattered light collected by the first photodetector, and a corresponding degree of bacterial growth in the sample; repeating, by the processor, the determining step at a series of pre-determined intervals; determining, by the processor, changes in the degree of bacterial growth in the sample as a function of time; and determining, by the processor, susceptibility of the bacteria in the sample to the drug used to dose the sample based on the determined changes in degree of bacterial growth in the sample as a function of time. In some embodiments of this and any other aspect of the disclosure, scattered light is detected in the range of scattering angles between +/−5 and +/−20 degrees relative to the incident beam axis.

It will be appreciated that the various features and the associated benefits/advantages that were described above in relation to the device and/or system, are equally applicable in relation to the method set out above.

For example, in some embodiments, the sample container comprises a plurality of detection chambers, at least two of the plurality of detection chambers containing a sample dosed with a different drug, and the method comprises: sequentially locating each of the plurality of detection chambers containing the drug-dosed sample in the light emitted along an incident beam axis; carrying out each subsequent step of the method in respect of each of the plurality of detection chambers; and determining the relative susceptibility of the bacteria in the samples to the respective drugs used to dose the samples to identify the most effective drug for use in a therapeutic treatment regime.

In some embodiments, the sample container comprises a plurality of detection chambers, at least two of the plurality of detection chambers containing a sample dosed with the same drug at different concentrations of drug, and the method comprises: sequentially locating each of the plurality of detection chambers containing the drug-dosed sample in the light emitted along an incident beam axis; carrying out each subsequent step of the method in respect of each of the plurality of detection chambers; and determining the relative susceptibility of the bacteria in the samples to the respective concentrations of the drug used to dose the samples to identify the most effective drug concentration for use in a therapeutic treatment regime.

Suitably, the method may further comprise: collecting, by a second photodetector, non-scattered light passing through the or each detection chamber parallel to the incident beam axis; and comparing an intensity of the non-scattered light collected by the second photodetector with an intensity of the scattered light collected by the first photodetector in respect of the same detection chamber.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

The above and other aspects of the disclosure will now be described, by way of example only, with reference to the accompanying drawings, in which:

FIGS. 1A and 1B show perspective front and back diagrams respectively of a device for determining susceptibility of bacteria in clinical samples to various drugs according to embodiments of the disclosure;

Figure 2:
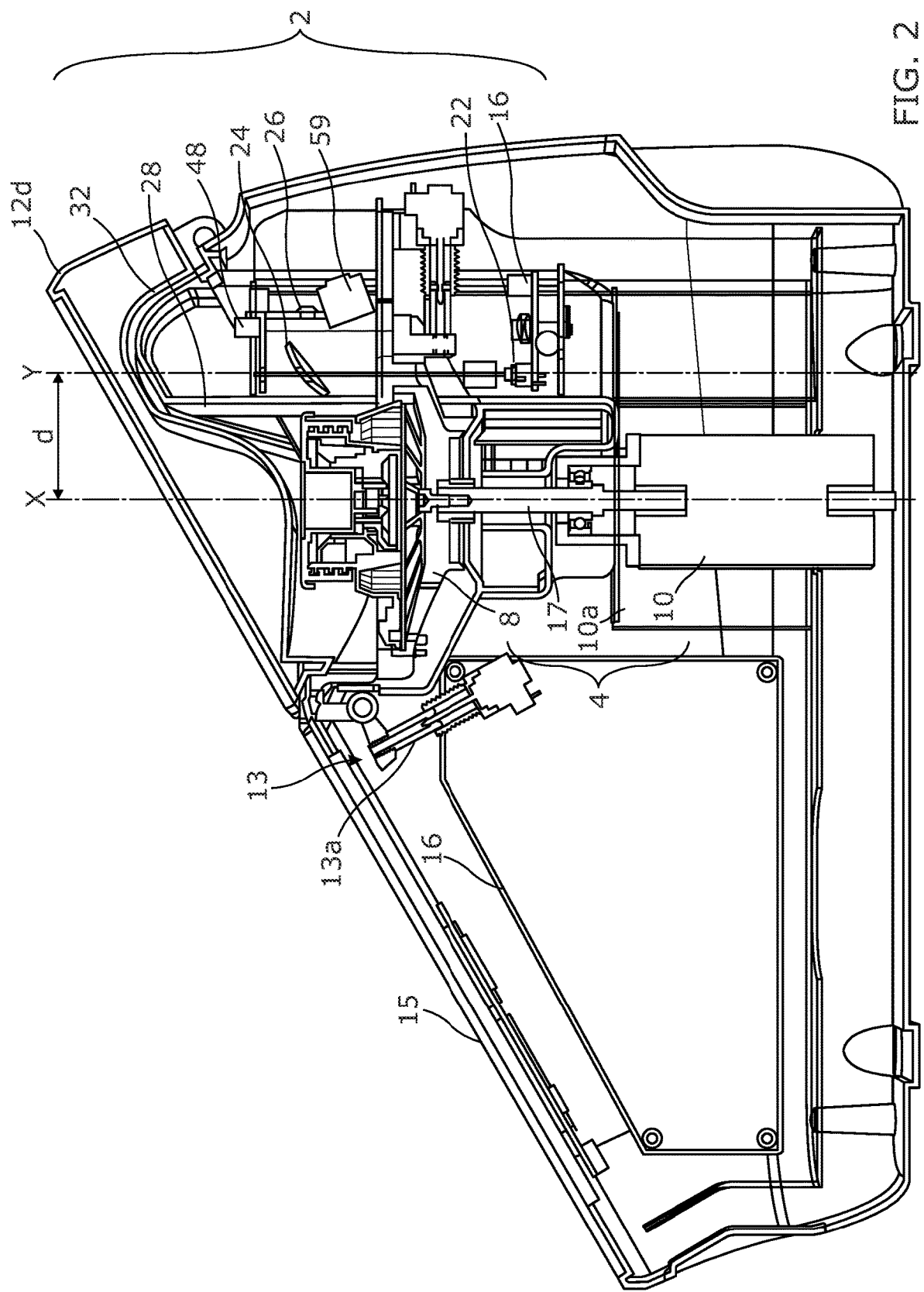
FIG. 2 shows a vertical cross-sectional diagram of the device of FIG. 1.

In the drawings, like features are denoted by like reference signs.

DETAILED DESCRIPTION

Specific examples and embodiments of the disclosure will now be described in which numerous features will be discussed in detail in order to provide a thorough understanding of the concepts defined in the claims. However, it will be apparent to the skilled person that the disclosure may be put into effect without all of the specific details and that in some instances, well known methods, techniques and structures have not been described in detail in order not to obscure the disclosure unnecessarily.

FIG. 1 shows front perspective (FIG. 1A) and back perspective (FIG. 1B) diagrams respectively of a device 1 that may be used according to embodiments of the disclosure, to provide a portable, self-contained and integrated module that may be utilised in point-of-care testing. In such cases, clinical samples (e.g. urine, blood etc.) from a patient or subject may be tested using the device to determine the susceptibility of bacteria in the sample to different types and concentrations of drugs. As will be described subsequently, this device 1 enables a particularly effective drug and treatment regimen to be ascertained and implemented quickly—i.e. within an hour or so—such that the patient can be provided with an effective treatment regimen for an infection far more quickly than would be possible by reliance on the prior art detection and diagnosis devices.

With reference to at least FIGS. 1 and 2, the device detects and measures the amount or intensity of light scattered by particles, particularly bacteria, in a clinical sample as a function of time, which thereby enables a corresponding determination of the representative amount or concentration of bacteria in the sample over time. The device 1 comprises an optical apparatus or arrangement 2; and a sample positioning mechanism 4. These two components are configured to interact with a removable sample container 6 containing the clinical sample under analysis in order to enable the above-mentioned determination of the representative amount or concentration of bacteria to be carried out.

Specifically, the sample positioning mechanism 4 is configured to engage with and support the sample container 6 in such a way that at least a portion of the sample container 6 is optically coupled or linked with components of the optical apparatus 2. In more detail, the sample positioning mechanism 4 comprises a sample carousel or sample carrier 8, and an operatively-coupled motor 10, for example a BLDC (Brushless DC) motor or other similar driving mechanism, which controls movement of the sample carousel 8 (and thereby of the engaged sample container 6). In use, when the sample container 6 and the optical apparatus 2 are optically coupled, the optical apparatus 2 is configured to illuminate a portion of the clinical sample contained within the sample container 6. The optical apparatus 2 is also configured to detect and measure light scattered by bacteria particles in the illuminated clinical sample portion. The detected scattered light intensity may then be analysed to ascertain properties of the bacteria in the sample, in particular the relative bacterial amount or concentration in the sample as a function of time.

The device 1 comprises an outer casing or housing 12 that contains the other components of the system 2 within it. In the illustrated embodiment, the housing 12 comprises a base 12a upon which the other device components are mounted; front 12b and rear 12c body portions that provide the walls of the housing 12; and a movable/detachable lid 12d. In the illustrated embodiment, the lid 12d is hingedly attached to the rear body portion 12c; although, of course, other attachments mechanisms may be used. The lid 12d together with the body portions 12b, 12c and the base 12a, form an enclosure that contains within it the various device components when the device 1 is in use. It will however be appreciated that the various portions of the housing 12 may instead be provided in more or fewer parts than have been illustrated herein. The device 1 further comprises a closure/securing mechanism 13 that is used to maintain the lid 12d in a closed, locked position, for example after the sample container 6 has been inserted into the desired position within the device 1 and engaged with the sample carousel 8. The closure mechanism 13 comprises an actuator 13a positioned within the device housing 12 (shown in more detail in FIG. 2) that may be programmably actuated in the event that the lid 12d is to be opened.

The device 1 further comprises a temperature control module or arrangement 14 (highlighted in FIG. 3A) that is configured to maintain the temperature within the housing 12, and particularly in the region surrounding the sample container 6, within a preferred temperature range (e.g., around 36 to 38°, and more particularly around 36 to 37°). This temperature range is particularly desirable to promote and maintain the growth of the bacteria within the clinical sample at optimal growth conditions. In addition, the illustrated device also comprises a user interface 15 such as an interactive touchscreen display, via which a user of the device 1 may interact with and program various aspects of the device 1; view certain results; and/or monitor the progress of the analysis process. For example, details of the patient or subject may be entered by the user; measurement parameters may be displayed and altered using the interface; software updates for the device 1 may also be downloaded via interaction of the user with the user interface 15; measurement progress and various intermediate and end-results may also be displayed to the user via the user interface 15. Additionally, the user interface 15 may be used to provide instructions to the user to guide them through the various steps in the process of loading a sample into the sample container 6, and subsequently of correctly engaging the sample container 6 with the sample carousel 8.

Finally, the device 1 comprises one or more processors or processing units 16 that provide programmable control of the various device components (e.g., the optical apparatus 2, the sample positioning mechanism 4, the lid closure mechanism 13, and/or the user interface 15). In some embodiments, it will be appreciated that the control of specific functionality and components of the device may be partitioned/allocated to certain one(s) of these processing units 16. In such embodiments, the control of certain functionality requiring real-time monitoring and having associated safety implications (for example, relating to the optical apparatus 2 and temperature control arrangement 14) may be controlled by one processing unit 16; whilst control of certain functionality relating to user interfacing and connectivity (such as the user interface 15) may be controlled by a separate processing unit 16. Additionally, in some instances, the device 1 may be provided with side vents/openings (not shown) that can increase airflow and facilitate cooling of the processing units 16 to prevent an undesirable increase in temperature within the device 1.

Figure 9A:
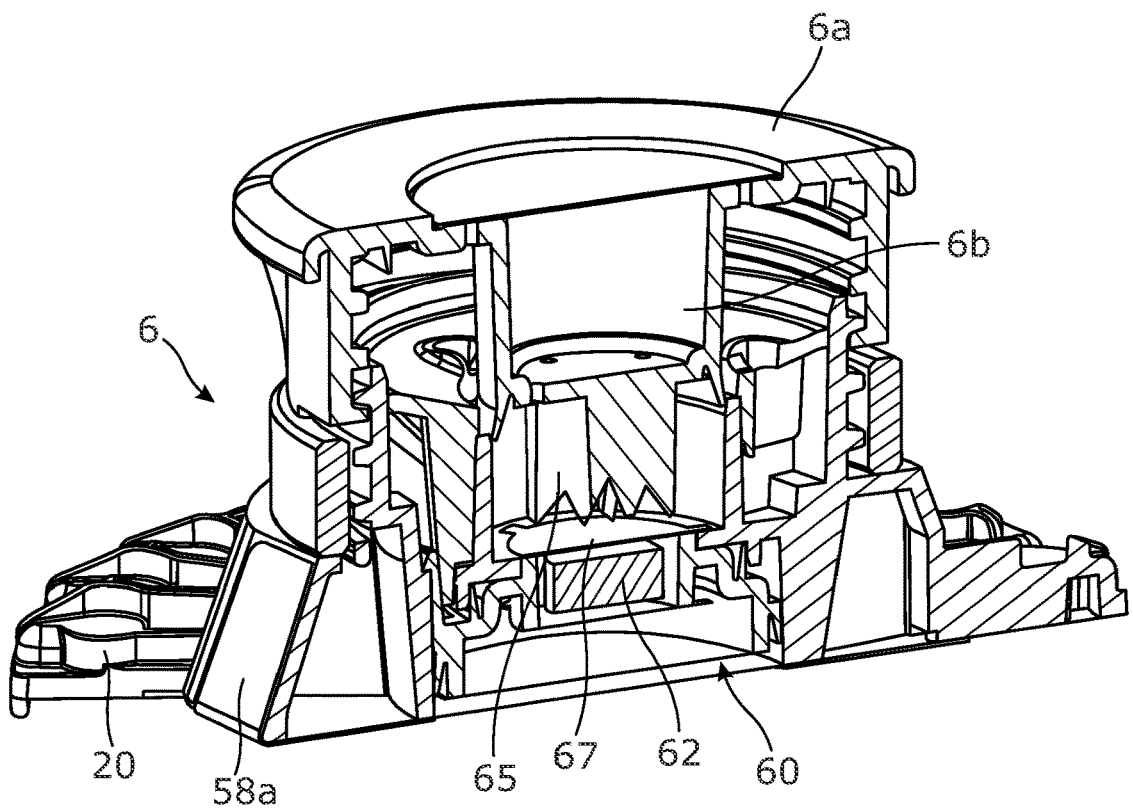
FIGS. 9A and 9B are vertical cross-sectional diagrams of a sample container that may be used in the device of FIG. 1 to analyse clinical samples.
Figure 9B:
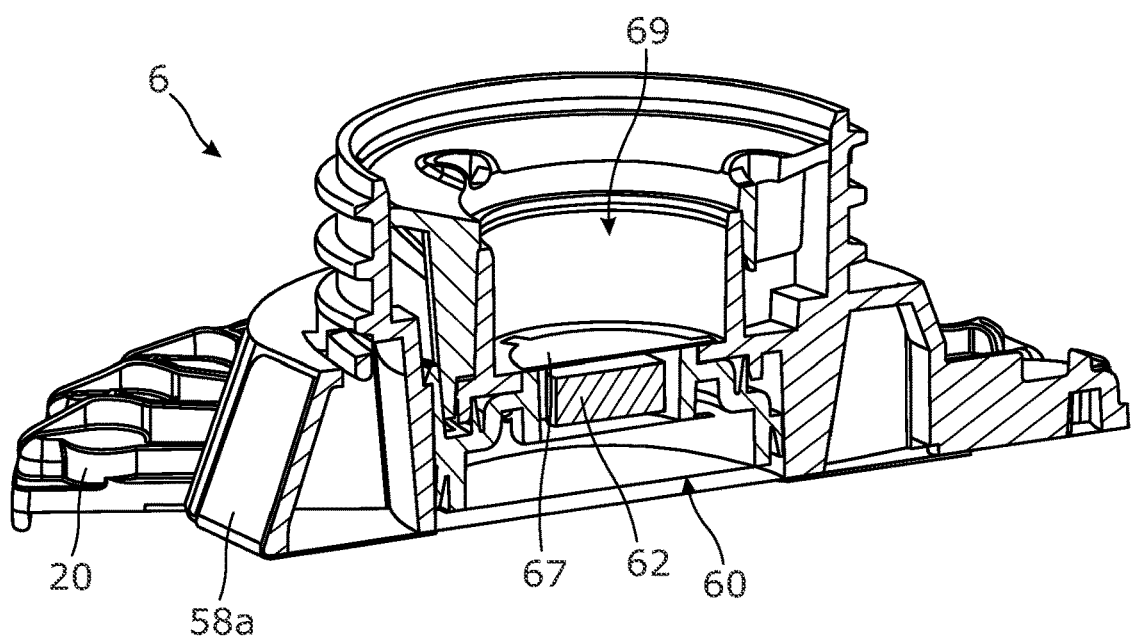
Figure 9C:
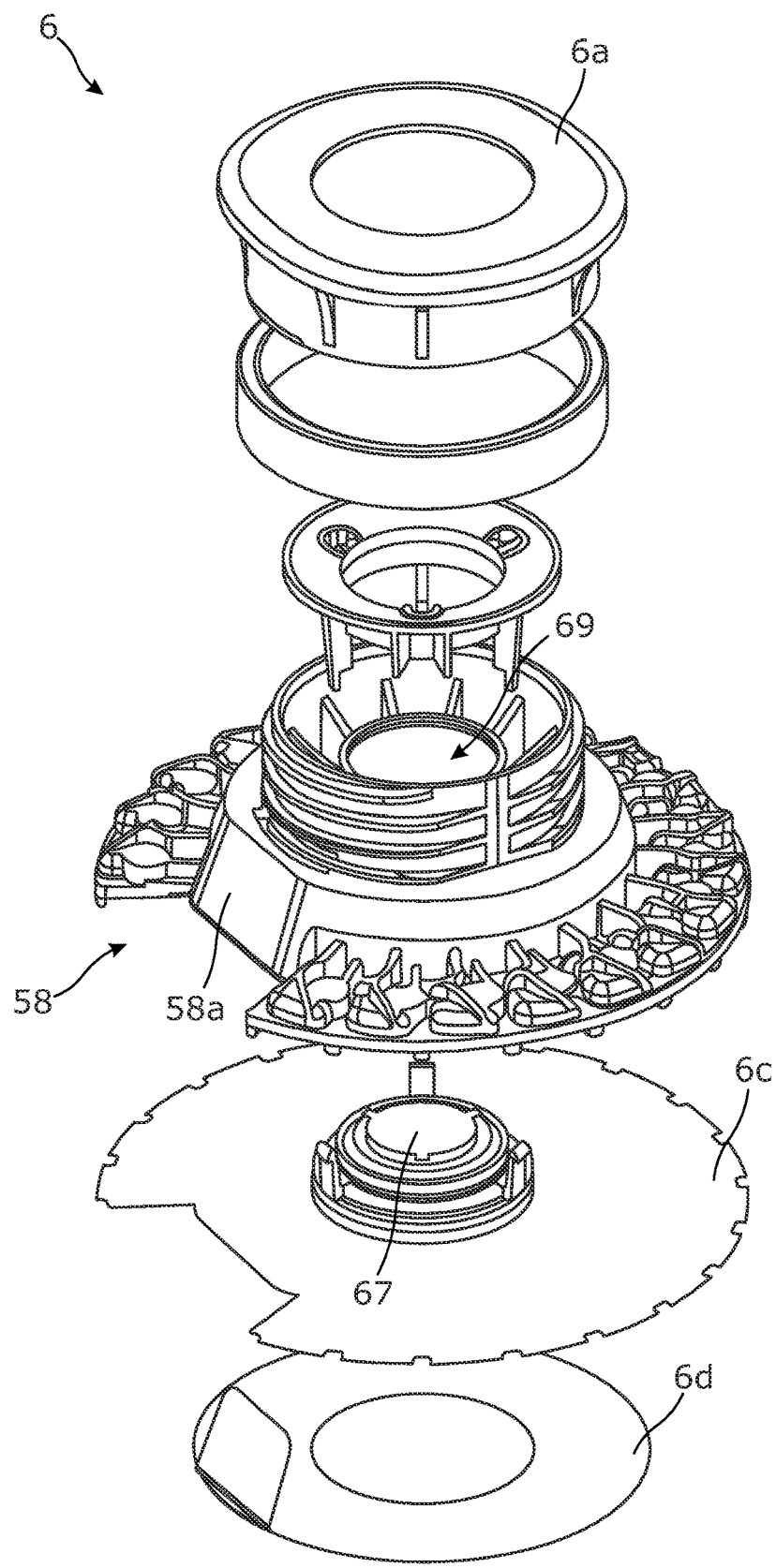
FIG. 9C shows an exploded view of another sample container that may be used in the device of FIG. 1.

As noted above, the sample container 6 corresponds to a separate component that is insertable into the device 1 in order to enable the required measurement and testing to be carried out. Typically, the sample container 6 may be intended to be and/or effectively provide a single-use component (i.e., usable to test one clinical sample). Such a component is therefore also referred to in the art as a 'consumable'. Further details regarding suitable and advantageous configurations of this consumable sample container 6 will be provided subsequently with reference to FIGS. 9 to 11; and additional detail is also provided in the Applicant's co-pending application entitled "Centrifugally motivated fluidic systems, device and methods", the contents of which are herein incorporated by reference in their entirety or to the extent applicable under national law.

Further details of the configuration of the various components of the device 1, and the interactions between these components, will now be provided with reference to FIGS. 2 and 3.

Specifically, as may be seen in these figures, the motor 10 is mounted to and supported by the base 12a of the housing 12; the motor 10 also effectively forms a supporting base upon or to which many of the remaining components of the device 1 are mounted. The sample carousel 8 is substantially circular in shape, and is mounted above and connected to the motor 10 via a rotatable shaft 17 that extends along a vertically-extending axis 'X' which passes through the centre of the sample carousel 8. Rotational movement of the sample carousel 8 about a central axis 'X' can thereby be driven by the motor 10.

The sample carousel 8 comprises a plurality of openings 18 provided at radial intervals around the sample carousel 8. According to the depicted embodiment, the openings 18 are located radially about an outer portion of the sample carousel 8 (these openings are shown in greater detail in FIG. 12A). The sample container 6 preferably comprises a corresponding plurality of detection chambers 20 (shown more clearly in FIGS. 9 and 10) provided at the same radial intervals around the sample container 6, and are each configured to contain a portion of the clinical sample that is to be analysed. The openings 18 in the sample carousel 8 are arranged such that, when the sample container 6 correctly interfaces and/or engages with the sample carousel 8, the location of each one of the plurality of openings 18 is aligned with and corresponds to the location of one of the plurality of detection chambers 20 provided within the sample container 6. As such, the detection chambers 20 can be located in any appropriate location of the sample container 6, for example, in an outer region thereof. As the skilled person will appreciate, the alignment between each opening 18 and corresponding detection chamber 20 should be suitable to allow light from a light source (as described below) to pass through the an opening 18 into a respective detection chamber 20. This interface between sample container 6 and sample carousel 8 is described in greater detail with reference to FIG. 12A.

The optical apparatus 2 comprises a light source 22 and collimating optics (not shown); a light collector or light collection arrangement 24; and at least one photodetector 26. The light source 22 emits light along an incident beam axis 'Y' and illuminates the sample portion(s) present in the detection chamber(s) 20 of the sample container 6. The light collector 24 collects light scattered in a forward direction by bacteria particles within the sample. Beneficially, the light collector 24 collects light scattered between the angles of around +/−24 degrees, around +/−20 degrees, or around +/−16 degrees from the incident beam axis Y, more specifically light scattered between the angles of +3 and +24 degrees and −3 and −24 degrees; +4 and +20 degrees and −4 and −20 degrees; and +5 and +16 degrees, and −5 and −16 degrees on either side of the incident beam axis Y (e.g. in a ring of particular radius about the light beam). Even more specifically, the light collected may be scattered between the angles of +4 and +16 degrees, and −4 and −16 degrees on either side of the incident beam axis Y. It will be appreciated that minor differences due to the curvature of the light collector 24 may mean that scatter is collected over slightly different angular ranges on either side of the incident beam axis Y (for example, between around 3 and 16 degrees on one side, and between 4 and 16 degrees on the other side). It will of course be appreciated by the skilled person that light scattered over even smaller angles (i.e., less than +/−3 or 4 degrees on either side of the incident beam axis) may also be collected; however this would increase the proportion of non-scattered incident light that is collected by the light collector 24. The width of the incident light beam could be reduced to allow light scattered at even smaller angles to be collected without including too great a proportion of the non-scattered light; however, this will in turn result in illumination of a smaller amount of the sample, which will reduce the amount of scattered light produced. There is hence a balance to be maintained in this regard, as will be discussed in greater detail subsequently. The collected scattered light is directed to the photodetector 26 by the light collector 24, where, for example, the intensity of the collected scattered light is analysed to ascertain relative bacterial amount or concentration of the sample in the detection chamber at a given point in time as a function of the amount of scattered light detected. The various components of the optical apparatus 2 are mounted to a support plate or structure 28 to form an optical 'tower' that, in the depicted embodiment. extends substantially vertically upwards from, and is supported by, the motor 10 or a housing 10a thereof. However, it will be appreciated that the mounting of the optical 'tower' 28 may be separate or de-coupled from the motor 10 and its housing 10a, so as to isolate the optical apparatus 2 from any vibrations that may be generated by the motor 10. In either case, this optical tower 28 structure is therefore also substantially perpendicular to the plane in which the sample carousel 8 and sample container 6 rest when in use. The incident beam axis 'Y' of the light emitted from the light source 22 is therefore parallel to, but laterally offset from, the rotational axis 'X' of the sample carousel 8 by a distance 'd'.

The lateral offset 'd' between the rotational axis X and the incident beam axis Y corresponds substantially to the radial distance of the (centre of the) detection chambers 20 from the centre of the sample container 6, and also to the radial distance between the centre of the sample carousel 8 and a region of the openings 18 provided within the platform. The support structure 28 for the optical apparatus 2 has a gap or cut-out 30 provided in it which is located (somewhere in the vertical plane) between the light source 22 and the light collection arrangement 24, and in the plane of the sample carousel 8; this cut-out 30 is sized and located to receive a radially-outer portion of the sample carousel 8 within it. As such, this received portion of the sample carousel 8 (and hence a corresponding portion of the sample container 6 when it is engaged with the sample carousel 8) may extend into and through the support structure 28 and optical tower and thereby intersect with the incident beam axis Y of the light emitted from the light source 22. Indeed, the sample carousel 8, support structure 28, optical apparatus 2 and sample container 6 are designed and adapted such that, in use, the light emitted by the light source 22 passes through one of the openings 18 of the sample carousel 8, and subsequently enters the corresponding detection chamber 20, thereby enabling the sample portion contained within that detection chamber 20 to be illuminated and analysed.

As a result, when the sample container 6 is engaged with the sample carousel 8, each of the detection chambers 20 of the sample container 6 are locatable in turn in the incident beam axis 'Y' via rotation by the motor 10 of the sample container 6 through the beam path of the light from the light source 22. Scattered light from the bacterial particles in the portion of the sample that is contained in each detection chamber 20 can therefore be collected and measured in turn by the optical apparatus 2. In some embodiments, by 'measured' it is meant to quantitatively assess the amount of light/intensity of light that is scattered by bacteria in the sample; whereas in other embodiments a qualitative assessment of the relative amount of scatter caused by samples in different sample chambers may be performed.

In the depicted embodiment, the optical apparatus support structure 28 comprises an upper (overhanging) cover portion 32 which covers (and may also provide some supporting functionality for) some of the components of the optical apparatus 2—for example, the light collection arrangement 24 and the photodetector 26. The upper cover 32 also provides the additional useful functionality of preventing unscattered light travelling along the substantially vertical incident beam axis 'Y' from exiting the device 1, or from accidentally reaching the user of the device 1 (e.g., in the event that the lid 12d of the housing 12 were to be removed whilst the light source 22 is emitting light). Additional detail regarding various configurations of the optical apparatus 2 will be provided subsequently with reference to FIGS. 4 to 7.

Turning now to the temperature control module 14, as may be seen from FIGS. 2, 3A, 3B and 3C, this portion of the device 1 is also mounted above and supported by the motor 10 and its housing 10a, and comprises at least one heating element 34 and a circulation arrangement 36. Each heating element 34, for example a heating coil, or an arrangement/plurality of heating coils, may be located within a corresponding compartment or chamber 38 that is positioned below the sample carousel 8. In the illustrated embodiment, a pair of heating elements 34 is provided (see FIG. 3A), located in a plane below the sample carousel 8 and above the motor 10: each of the pair of heating elements 34 positioned on a respective side of the optical apparatus support structure 28. As the skilled person will appreciate, each heating element 34, in use, heats the air in its vicinity; this heated air rises towards the underside of the sample carousel 8 and its associated sample container 6. The circulation arrangement 36 then circulates the air more widely though the device housing 12, such that a substantially constant flow of heated air passing over and around the sample container 6 is maintained; the temperature of the contents of the sample container 6 is hence kept within the desired (optimal) temperature range in order to promote rapid bacterial growth and multiplication. In the illustrated embodiment, the circulation arrangement 36 comprises a pair of recirculation ducts 40 having air intakes 40a that are located at a level above the sample container 6, and air outflows 40b that are located at a level below the sample carousel 8. In this way, air temperature inside the device can be rapidly adjusted as necessary. The circulation arrangement 36 also comprises one or more associated fans 42 or other mechanisms to drive airflow around the circulation arrangement 36. Specifically, in the illustrated embodiment, each heating element 34 has a fan 42 associated with it to drive circulation of the air heated by that heating element through the circulation arrangement 36.

Figure 3A:
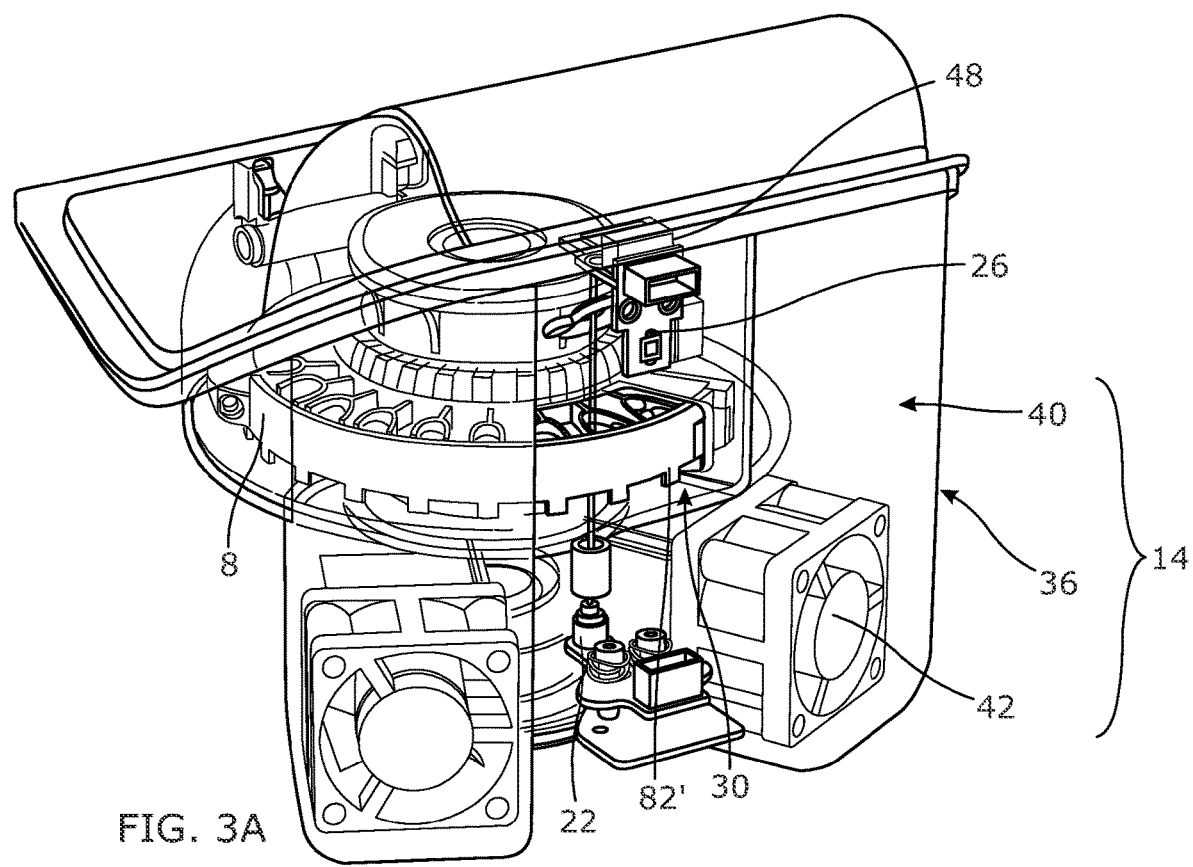
FIGS. 3A and 3B are perspective diagrams of a portion of the device of FIG. 1.
Figure 3B:
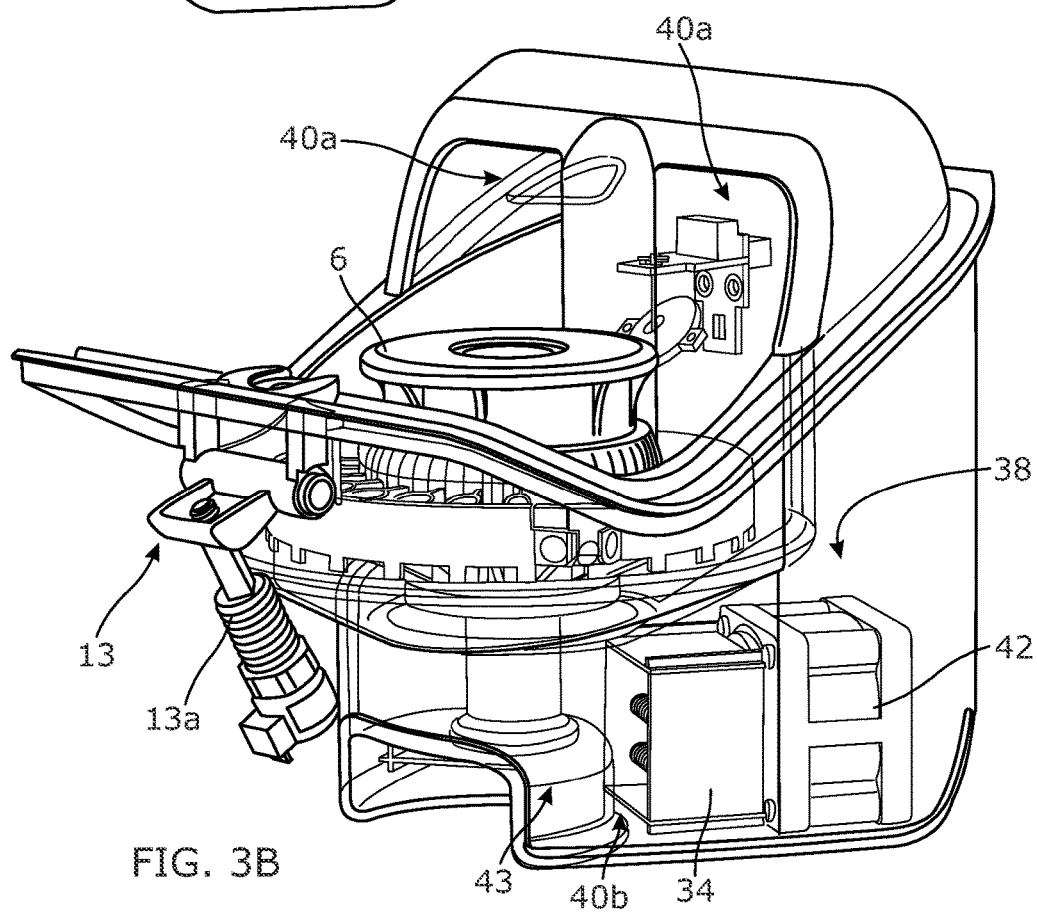
Figure 3C:
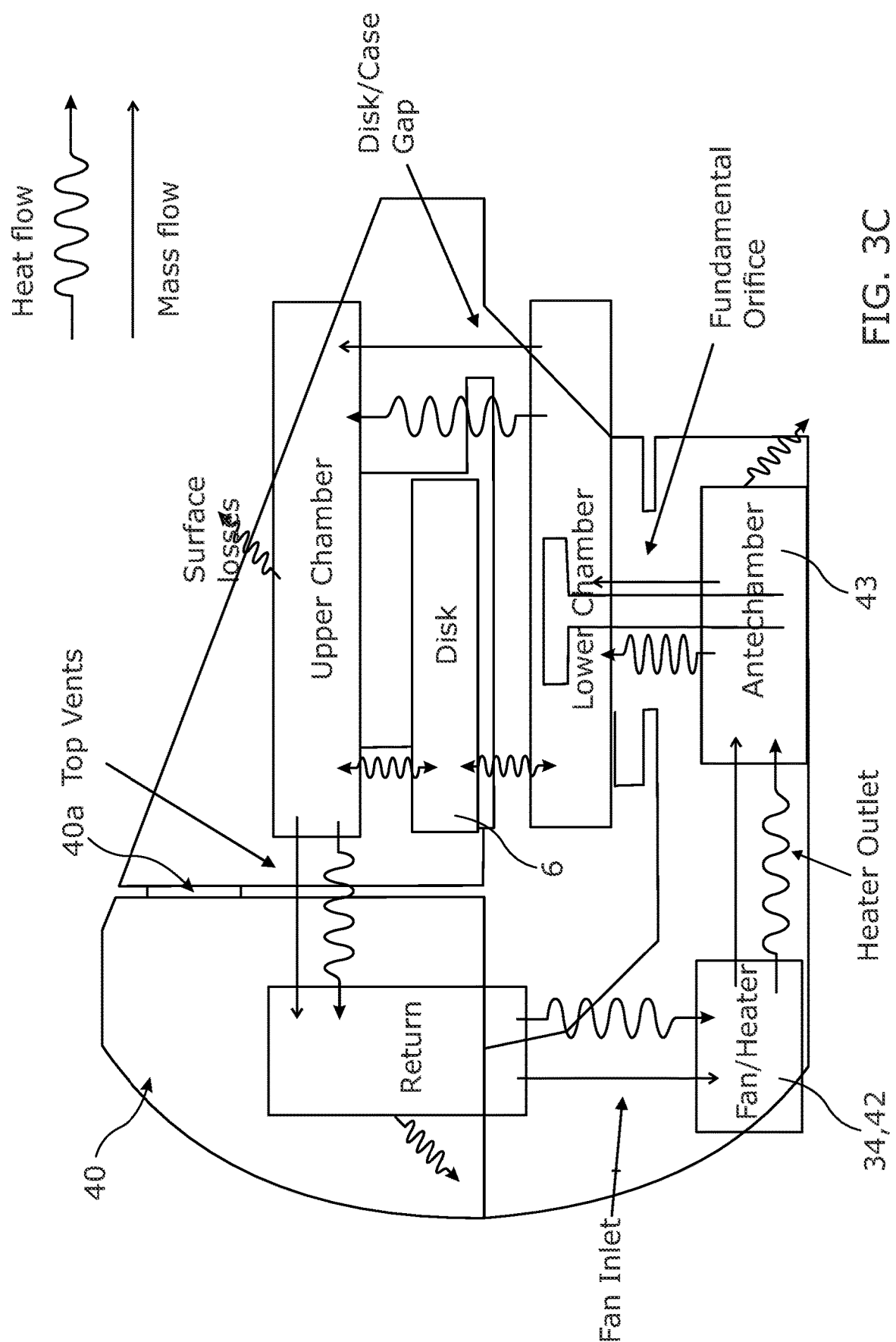
FIG. 3C illustrates the internal airflow and temperature gradient of the portion of the device shown in FIGS. 3A and 3B.

FIG. 3C illustrates the movement of air achieved via the temperature control module 14 in greater detail. Each heating element—fan pair is located at the base of its corresponding recirculation duct 40. The fans 42 drive a constant stream of air through/across the associated heating elements 34; this heated air is then driven out of the corresponding outflows 40b of the recirculation ducts 40 into an antechamber or intermediate compartment 43 below the sample carousel 8. The heated air then rises upwards through the device and flows across and around the sample container 6, cooling in the process. This relatively cooler air then enters the air intakes 40a of the recirculation ducts 40 to replace the air that was driven out by the fans 42 and flows back down to the heating element—fan pair. As the recirculation ducts 40 are located on either side of the optical apparatus 2, the material used to create these ducts 40 is suitably moulded and configured to prevent the heated air from causing overheating of the optical apparatus components. This helps to prevent any undesirable warping or malfunction of these components, or prevent any erroneous measurements from being taken due to excessive heat.

It will be understood that while the device is depicted in FIGS. 3A, 3B and 3C as having a pair of heating elements each comprising a plurality of heating coils, one or more heating elements may be suitable according to preferences and design. Moreover, while a plurality of heating coils may be advantageous in providing rapid heating of the air within the chamber in this embodiment of the invention, one heating coil may be used, and, alternatively, many other forms and configurations of one or more heaters are available to the skilled person and may be selected according to preferences. Similarly, while the present device is depicted having a pair of fans (one assigned to each heating element) in order to push warm air around the inner chambers of the device, in embodiments a fan is not necessary, for example, the flow of air caused by spinning of the sample container 6 and sample carousel 8 is capable of creating movement of heated air towards and around the sample container 6.

Provision of an effectively mirror-arrangement pair of heating elements 34 and fans 42, each pair having their corresponding recirculation ducts 40, on either side of the sample carousel 8 has been demonstrated to be particularly useful in maintaining a good balance of heating within the device 1. It also compensates for any asymmetry in heating that might be created by the continued rotation of the sample container 6 in a particular direction. Furthermore, heating the sample container 6 in this 'bottom-up' manner (i.e., the air is heated and rises quickly up through the sample container 6) enables quicker and easier heating of the sample portions contained within their individual detection chambers, without wasting excessive amounts of heat (and heating time) in also heating up the material of the sample container 6 itself. Thus, where the sample container 6 includes a plurality of samples each in a different detection chamber 20 around the perimeter of the sample container 6, heating of sample within each detection chamber 20 is beneficially consistent. In some instances, maintenance of the desired consistent temperature of the samples in the sample container 6 may be carried out with the aid of a temperature measurement device (such as an Infrared or IR thermometer) located within the device 1, for example above or near the sample container 6.

Figure 4:
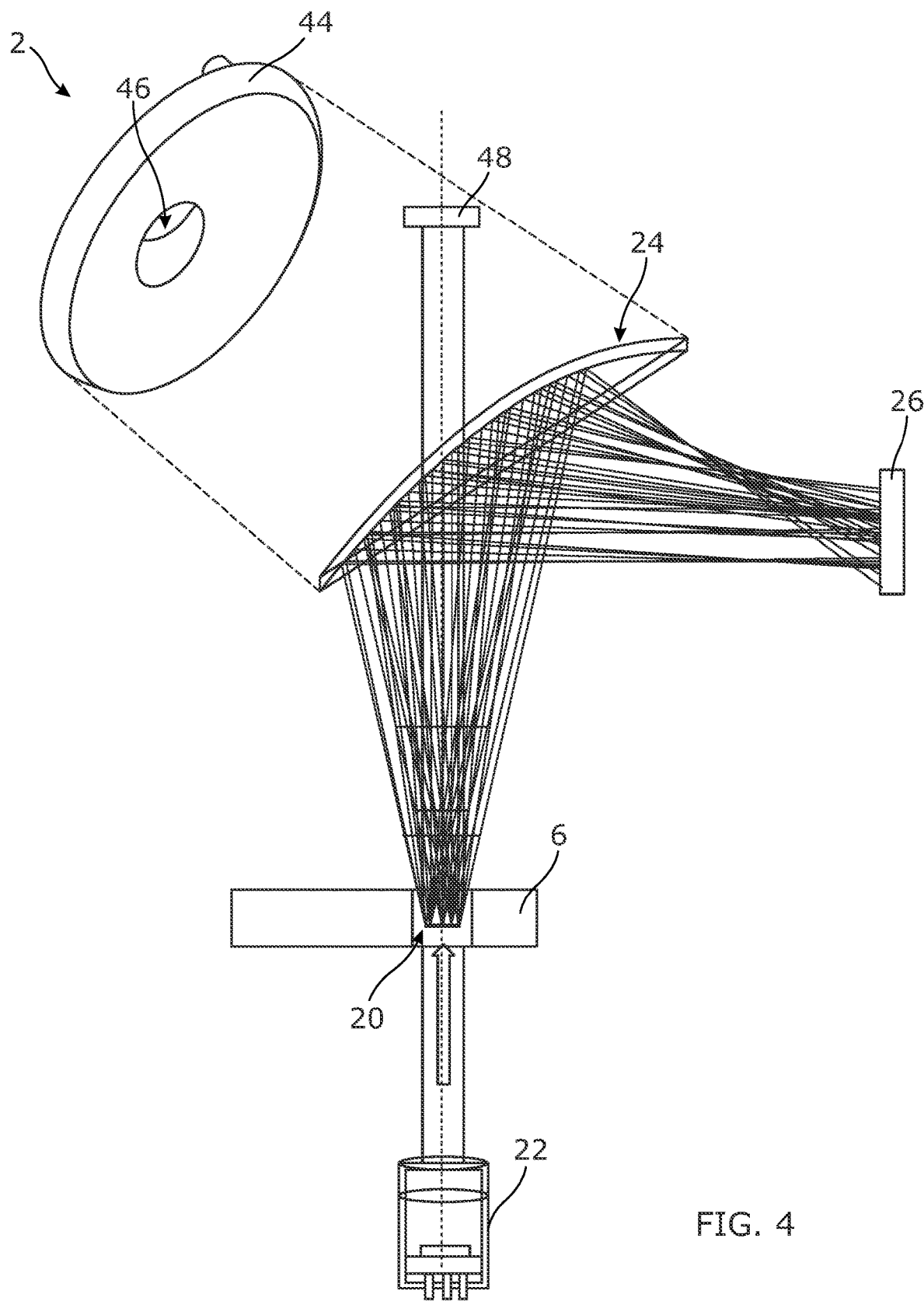
FIG. 4 is a schematic diagram of an optical apparatus arrangement used in the device of FIG. 1 according to an embodiment of the disclosure.

FIG. 4 illustrates details of an example arrangement of optical components in the optical apparatus 2. In this arrangement, the light source 22 corresponds to a laser module having a laser diode that is used to generate light at a specific wavelength (for example, visible red light in the wavelength range between 620 nm and 780 nm, and more particularly around 635 nm) for illuminating the sample portions contained in the detection chambers 20. It is noted that the above wavelengths have been envisaged for use in relation to the analysis of urine samples; however depending on the nature of the sample that is to be analysed, the wavelength of light used may differ. For example, near infrared wavelengths (between about 650 nm and about 1350 nm) could be utilised in relation to blood samples. The laser diode is connected to a signal generator (not shown) that is adapted to control a modulation frequency and amplitude of the laser output. The photodetector 26 corresponds to a photodiode which is connected to a lock-in amplifier (also not shown); the lock-in amplifier is in turn connected to the signal generator for the laser diode. This enables the photodiode to isolate and filter out a specific received signal having a frequency corresponding to the modulation frequency generated by the signal generator for the laser diode. This allows noise signals at other frequencies (e.g., background noise, electrical noise) to be filtered out, thereby improving the signal-to-noise ratio obtainable using the optical apparatus 2. These components may be controlled via one or more of the system's processors 16, which may for example take the form of one or more Printed Circuit Boards (PCBs) or other types of micro-controllers.

The light collector 24 in this example comprises a reflector or reflective surface that, in the depicted embodiment, is mounted to the support structure 28 so as to extend across the incident beam path. Specifically, the light collector 24 of FIG. 4 corresponds to a curved concave elliptical mirror 44 having an off-centre hole, aperture or opening 46 provided within it. The mirror 44 is mounted to the support structure 28 such that the hole 46 is aligned with the incident beam axis 'Y', thereby allowing non-scattered light exiting the detection chamber 20 and travelling along the beam axis Y to pass directly through the mirror 44 substantially non-deflected; this non-scattered light is hence prevented from reaching the photodetector 26. Furthermore, the mirror 44 is arranged at such an angle and is of such a size that the light scattered in the forward direction by the particles in the sample, and particularly the light scattered within the range of angles between about +4 and +16 degrees, and about −4 and −16 degrees of the incident beam axis Y, is reflected by the mirror 44 and towards the photodetector 26. In some other embodiments, the light reflected by the mirror 44 towards the photodetector 26 may be in the range of angles between about +5 and +16 degrees, and about −5 and −16 degrees of the incident beam axis Y.

It will be appreciated by the skilled person that when considering the sensitivity of the scattered light detection, there is an interplay between the size of the light collector (mirror) aperture 46; the width of the light beam from the light source 22; and the width (diameter) of each detection chamber 20 of the sample container 6 through which the light beam passes. A balance needs to be struck between these values to optimise the scattered light detection sensitivity. Increasing the width of the light beam from the light source 22 increases the amount of (bacteria) particles in the sample which are illuminated by the light beam; this consequently increases the amount of scattered light produced in any given scattering event which can be detected. However, when carrying out measurements of scattered light emanating from a detection chamber 20, increasing the amount of time that the entire width of the light beam illuminates the sample within the detection chamber 20, provides a longer 'clean' measurement path/zone of the light beam through the sample (away from the walls of the detection chamber 20 which may cause internal scattering that could decrease the accuracy with which detection of scattered light from the sample is carried out). Hence, whilst increasing the light beam width increases the detection sensitivity, the light beam width should nevertheless remain smaller than the width/diameter of the detection chamber 20 to balance these two factors. Furthermore, it will also be appreciated that configuring the system such that the diameter of the aperture 46 in the light collector (mirror) is as close as possible to the width of the light beam will enable as much scattered light as possible to be collected and directed towards the photodetector 26, whilst minimising the amount of non-scattered light collected. However, if the width of the light beam is too closely matched to the diameter of the aperture 46, slight deviations in the path travelled by the light beam over the course of the measurements (e.g., due to vibrations or machining tolerances of the components in question) may adversely affect the alignment of the light beam with the aperture 46; this will hence have a corresponding negative impact on the detection sensitivity.

In a particular embodiment, it is envisaged that the diameter of the detection chamber 20 is around 4 mm, in which case light beam widths of between around 1 mm and 3 mm (and more particularly between 1.5 mm and 2.4 mm) would provide a good balance between the number of bacteria particles illuminated and the length of the 'clean' measurement path within the detection chamber 20. In such an embodiment, where the width of the aperture 46 is selected to be around 3 mm, a light beam width of around 1.5 mm for example would be suitable for use, as it also leaves sufficient margin between the aperture width and the light beam width to take into account machining tolerances and/or system vibrations. However, where the aperture 46 is enlarged (for example, 4 mm in diameter to match the diameter of the detection chamber 20), the light beam width used may also be correspondingly increased (for example to between around 2 mm and 2.4 mm).

Figure 8:
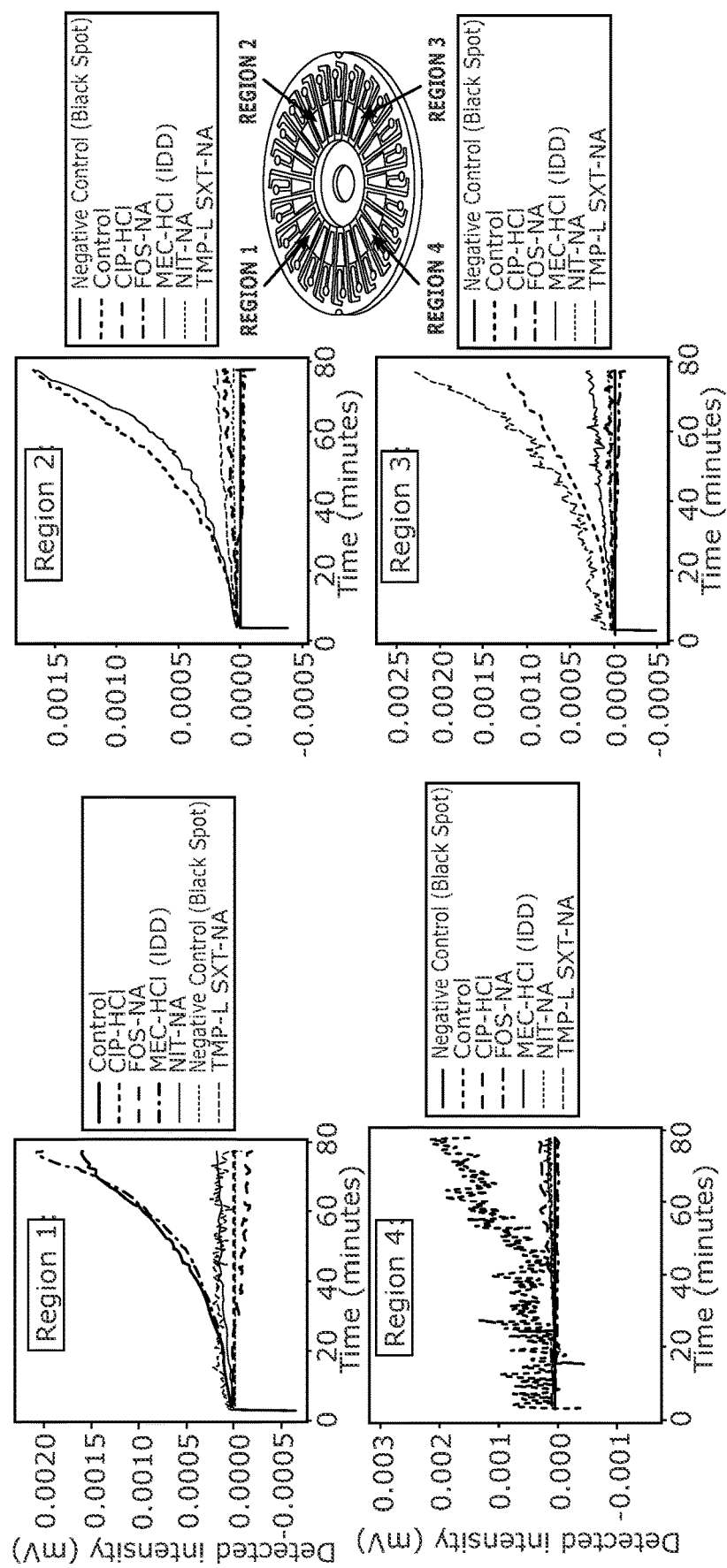
FIG. 8 shows different plots of detector intensity output as a function of time in the device of FIG. 1, illustrating the effects of different drugs on bacteria in a clinical sample.

In the arrangement of the depicted embodiment, concave, elliptical mirror 44 reflects the forward scattered light at the determined angles away from the incident beam axis Y (and by substantially 90 degrees relative to the incident beam axis Y) to be concentrated onto/focused on the photodetector 26. One or more of the system processors 16 is associated with the photodetector 26 and processes the detection signals generated by the photodetector 26 to calculate the intensity of the scattered light detected. A graph or plot of the detector output (which corresponds to the measured scattered light intensity as a function of time) may be generated; examples of such graphs are shown in FIG. 8. This graph and/or the data used to generate it may be displayed to the user via the user interface 15, for example as a substantially real-time indication of progress, at regular intervals; or as a final (summary) output once the analysis process for a given sample is complete.

As shown in FIG. 4, the system of this embodiment also comprises a second photodetector 48, aligned with the incident beam axis 'Y', but located on the opposite side of the light collector 24 from the sample and arranged to detect and measure the non-scattered light passing through the hole 46 in the mirror 44. This second photodetector 48 also corresponds to a photodiode that may be configured in substantially the same manner to that of the first (main) photodetector 28—i.e. the second photodetector 48 is connected to the signal generator of the light source 22 via a lock-in amplifier to ensure that the second photodetector 48 (and/or one of the processors 16 that is associated with the photodetector 48) is also able to filter out the desired laser signal frequency (and phase) from any noise signals that differ in frequency to that of the laser. Provision of this additional second photodetector 48 allows for a baseline measurement of the non-scattered laser light to be obtained. This baseline measurement may be compared with the scattered light intensity measured using the first (main) photodetector 26, which allows, for example, anomalies in the illumination to be detected; the laser stability may also be assessed and taken into account during analyses. It will be appreciated that in any of the embodiments of the disclosure, a second photodetector 48 may be omitted. In some such embodiments, a beam dump or other apparatus may be used to collect non-scattered light from the laser.

In some cases, the mirror 44 is manufactured via a customised moulding process to ensure that the appropriate size, shape and reflective properties are obtained. During such a process, the reflective surface of the mirror 44 may be created via for example (vapour) coating of the mirror surface with aluminium or enhanced aluminium. In some optional instances, the reflectivity of the mirror (at around 650 nm) should be more than 90% (e.g. at least 95% or 98%), and the surface roughness of the mirror should be less than 100 Å (e.g. less than 80 Å, less than 60 Å or even less than 40 Å. While the optical arrangement depicted in FIG. 4 is particularly beneficial in reducing the number of parts necessary to perform the disclosure, other optical arrangements may also be possible. For example, the customised concave elliptical mirror 44 of FIG. 4 may be replaced with a pair of reflective elements, for example, a first mirror that deflects forward scattered light onto a focusing lens or second concave mirror, which concentrates reflected light from the first mirror onto a photodetector 26. Additionally or alternatively, one or more additional concentrating components may be incorporated into the optical apparatus arrangement 2 in relation to or in association with the photodetector 26. For example, one or more concentrating components (such as a concentrating lens) may be arranged to from a 'concentrating cone' around the photodetector 26 to maximise the amount of scattered light that is collected by the photodetector 26.

Figure 5:
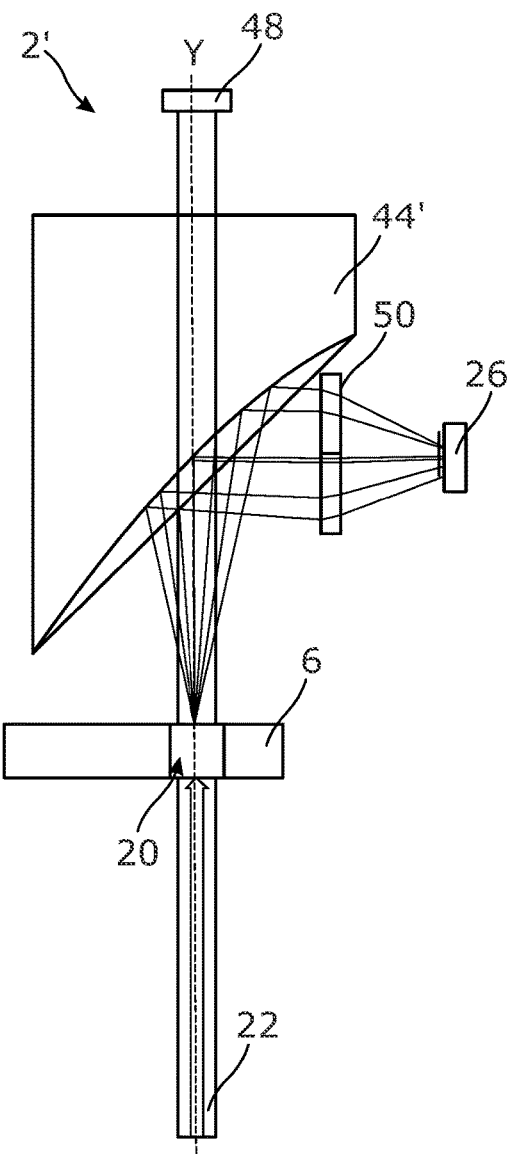
FIG. 5 is a schematic diagram of an alternative optical apparatus arrangement that may be used in the device of FIG. 1 according to another embodiment of the disclosure.

An alternative optical apparatus arrangement 2' is shown in FIG. 5, in which an off-the-shelf concave mirror 44' may be used rather than the customised specifically-shaped mirror 44' (although the reflectivity and surface roughness properties should be comparable). In this case, the curvature of the mirror 44' may not necessarily be configured to focus all (or at least substantially most) of the forward-scattered light from the sample interactions onto the photodetector 26. In such cases, an additional concentrating component 50 (e.g. a concentrating lens such as a Fresnel lens) may be introduced into the optical arrangement in the light path between the mirror 44' and the photodetector 26, to ensure that as much as possible of the forward-scattered light reflected by the mirror 44' is captured and focused onto the photodetector 26. This maximises the total amount of scattered light that can be obtained using the optical apparatus 2', which in turn also increases the sensitivity of the apparatus overall to detect smaller changes in the relative amount or concentration of bacteria in the sample overtime. In other embodiments, as indicated above, the lens 50 could be substituted for a second mirror configured to reflect light onto the photodetector 26. The additional concentrating component(s) mentioned above in relation to the optical apparatus arrangement 2 of FIG. 4 may also be incorporated into the optical apparatus 2' in addition to, or as an alternative to, the concentrating component 50 described above.

Figure 6:
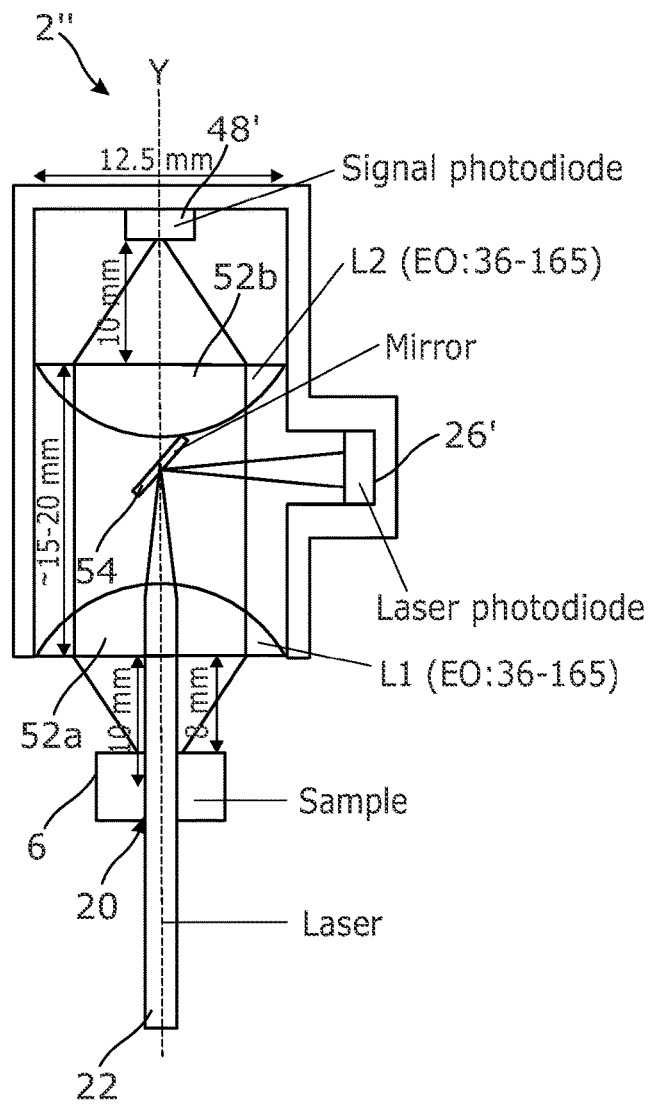
FIG. 6 is a schematic diagram of an alternative optical apparatus arrangement that may be used in the device of FIG. 1 according to another embodiment of the disclosure.

FIG. 6 shows another alternative optical apparatus arrangement 2" which has been envisaged that also separately collects scattered and non-scattered light—the beam paths of these two types of light are illustrated in the figure. In this alternative arrangement, the light collector 24 comprises a pair of condensing lenses 52a, 52b separated by a distance 'a' that is greater than the focal length of the first lens 52a and oriented such that the convex surfaces of the lenses are facing towards one another along the incident beam axis Y. In this configuration, any diverging beams of light incident on the first condensing lens 52a will be collimated into parallel light beams, that are also parallel to the incident beam axis Y. Such parallel beams of light will then, upon being incident on the second condensing lens 52b, be converged towards a point a further distance away along the incident beam axis Y. However, any parallel beams of light passing through the centre of the first condensing lens 52a (or within a region corresponding to light scattered by a maximum predetermined angle from 0°, e.g., up to 5°) will instead be converged to a point at the focal length of that lens 52a. In the illustrated arrangement 2", the light collector 24 further comprises a mirror 54 located at a position corresponding to the focal length of the first condensing lens 52a and sized and oriented to reflect only the light which reached the first lens at an angle of incidence of no more than the above maximum predetermined angle. Light which passed through the sample substantially without scattering will therefore hit the surface of the mirror before reaching the second condensing lens 52b and will be deflected away from the second lens 52b. In the depicted embodiment, the mirror 54 is angled (at substantially 45 degrees) relative to the incident beam axis Y (although other angles can at least be selected), and hence any light beams incident upon the mirror 54 are reflected by around 90 degrees to the incident beam axis Y and directed out of the main incident beam path; this light will hence not reach the second condensing lens 52b.

As was the case for the optical apparatus arrangements 2, 2' shown in FIGS. 4 and 5, the laser diode light source 22 in the current arrangement 2" of FIG. 6 emits light along the incident beam axis Y, which illuminates the sample in the detection chamber 20 of the sample container 6; bacteria within the sample scatter the incident light beam in a forward direction and over a corresponding relatively small angular range. In addition, as with the optical apparatus arrangements of FIGS. 4 and 5, two photodetectors are provided in the optical arrangement 2" of FIG. 6: a first 'off-axis' photodetector 26' is positioned to be angularly offset (by around 90 degrees) relative to the incident beam axis Y; and a second 'on-axis' photodetector 48' is positioned in alignment with the incident beam axis Y. However, in the optical arrangement of FIG. 6, the non-scattered light passing through and exiting from the detection chamber 20 in a parallel beam is focused onto the mirror 54 by the first condensing lens 52a, and thereafter onto the offset off-axis photodetector 26'. The forward-scattered light beams that are generated by the interaction of the incident light with bacteria in the sample are focused by the pair of collimating lenses 52a, 52b onto the on-axis photodetector 48'. This is in direct contrast with the arrangements of FIGS. 4 and 5, where it is the off-axis (main) photodetector 26 that detects the scattered light, and the on-axis photodetector 48 that detects the non-scattered baseline laser light.

By using one of the above-described optical apparatus arrangements 2, 2', 2", the device 1 is able to optimise/maximise the collection of light scatter useful in assessing properties and/or quantities of the bacteria in the sample. This is because the Applicant has appreciated that the majority (around 95%) of the light scattered as a result of such bacterial interactions, is scattered only over a relatively small range of angles on either side of the incident beam axis Y, for example between the angles of +/−20 degrees from the incident light beam axis Y (and more particularly between the angles of around 4 or 5 to 16 degrees on either side of the incident beam axis Y). Therefore, instead of requiring an integrating sphere light collector or other form of light collector that utilises multiple reflections and/or diffusion of scattered light to increase the collected intensity (including in some cases back-scattered light), a simplified light collection arrangement may be utilised that is configured to collect the light scattered over those identified angular ranges most relevant to assessing/measuring particles in a sample, and to direct/concentrate the collected light onto a photodetector.

Figure 7:
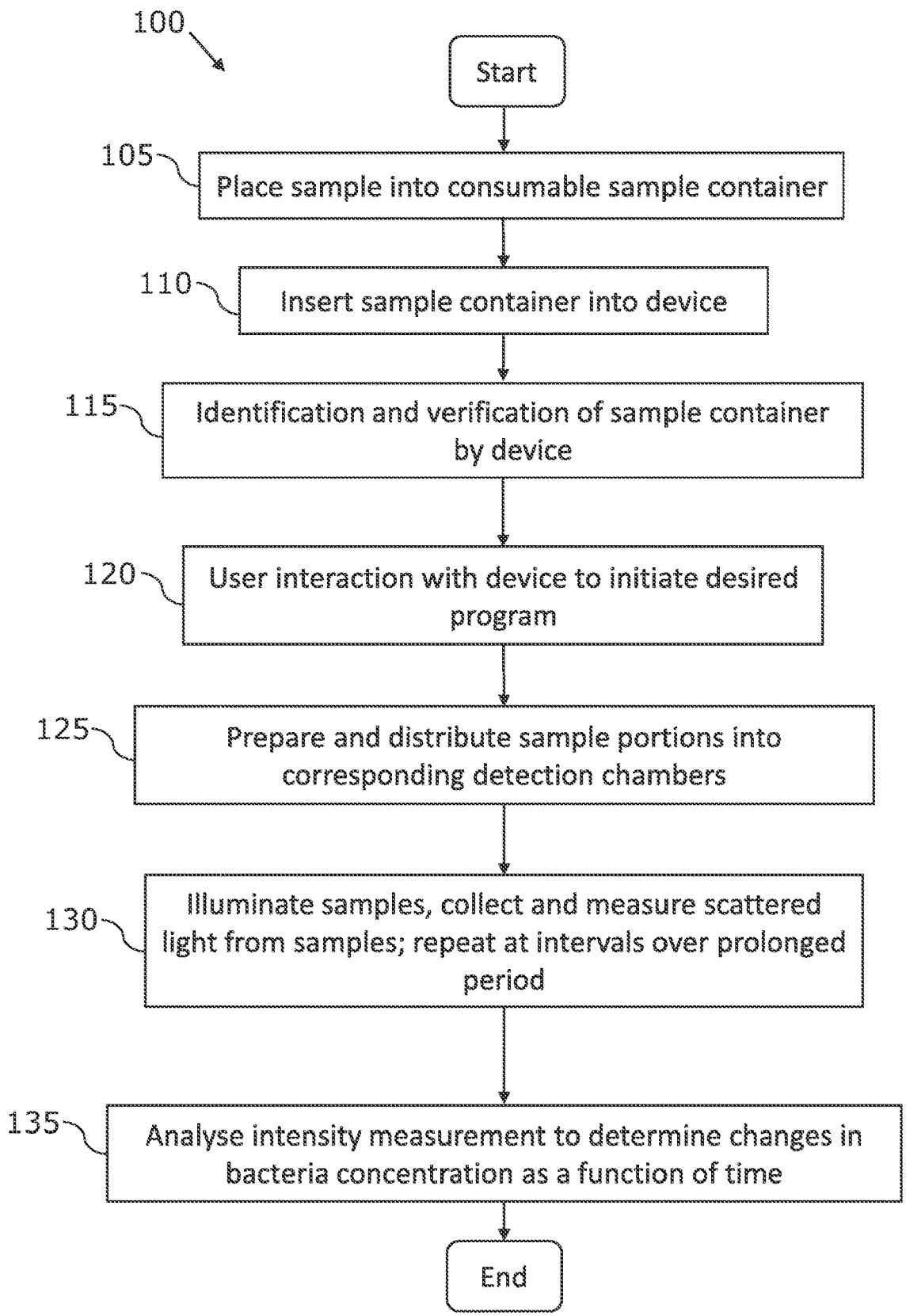
FIG. 7 is a flow diagram illustrating various steps of a method for determining drug susceptibility of bacterial in a clinical sample using the device of FIG. 1

A method of using the above-described device 1 will now be described with reference to FIG. 7.

To begin with, the clinical sample is placed securely in the sample container 6 by the user in Step 105, and the sample container 6 is then inserted into its appropriate location within the device 1 in Step 110. This involves correctly aligning the sample container 6 with the optical tower support structure 28 (e.g. aligning an indent or cut-out segment or other surface feature 58 of the sample container 6 with the support structure 28 or corresponding/complementary structure of the device 1) and engaging the sample container 6 with the sample carousel 8, for example, via a click-in/clip-in and pull-out mechanism. In some embodiments, this process may be guided by the user interface 15 (e.g., via a series of diagrams and corresponding written/spoken instructions). In some embodiments, the sample carousel 8 itself may also be removable to facilitate easy cleaning as required. The lid 12d of the device 1 is then closed and locked into place; and the user interacts with the user interface 15 in Step 120 in order to initiate the sequence of pre-programmed actions that are to be taken by the various components of the device 1 in order to perform the desired sample analysis.

Prior to these pre-programmed actions being performed, or in fact as part of these actions, the device 1 may be configured to identify in Step 115 the sample container 6 and determine information relating to that specific sample container 6, based on data provided on the sample container 6 itself or on packaging thereof. In some cases, this information may be contained within or be obtainable via a unique identification code provided on the sample container 6, which may include a unique identifier associated with the sample container 6 itself, a unique identifier associated with a particular batch of which the sample container 6 forms a part, and a use-by date for the contents of the sample container 6. This identification code may be provided in the form of an RFID tag or a barcode (e.g., a 2D barcode) that may be scanned by the device 1, either prior to the insertion of the sample container 6 (e.g., via a separate scanner associated with the device 1), or even after insertion of the sample container 6 (e.g., via a scanner integrated into the device 1). For example, an internal barcode scanner/reader 59 is shown (in the illustrated device of FIG. 2) as being mounted to an internal wall of the device housing 12. In this embodiment, the scanner 59 is mounted at a particular angle such that it is directed towards an identifying RFID tag or barcode located on the sample container. For instance, the barcode or other means of identification may be located on an angled portion 58a of the sample container 6 (e.g., positioned adjacent the cut-out segment 58 of the sample container 6 so that it can be read by the scanner 59 once the sample container 6 is inserted into the device 1—shown in FIGS. 9A and 9B).

Additional information may also be provided as part of or in addition to the identification code, for example details of the specific drugs provided within each of the detection chambers 20 of a given sample container 6, such that the analysis is performed with knowledge of the drugs that are being tested. Furthermore, details regarding software updates that may need to be implemented may also be included as part of the provided information; this enables the device 1 to easily and efficiently obtain information from the sample container 6 itself regarding the appropriate software updates and changes that may be required.

Additionally or alternatively, the unique identification code can be provided on the packaging of the sample container 6 (e.g. on a box containing one or a plurality of sample containers 6 of a particular batch), or may even be provided together with the packaging, for example in the form of a USB stick that is associated with the packaging and which has been pre-loaded with the relevant identification information. Advantageously, utilising the packaging or a separate USB stick to provide this information increases the storage space available to contain the data, thereby enabling more data to be provided within the identification code. In such a case, the device housing 12 may be provided with a port to receive and interface with the USB stick.

The device 1 may also be programmed to verify that the sample container 6 is one of an approved batch of containers that can be used with the device 1 (e.g., to identify any counterfeit or unauthorised sample containers and prevent them from being used with the device 1). In this regard, the sample container 6 may be provided with an identifying (anti-counterfeit) feature that is detectable by the device 1; this may be provided as part of, or in addition to, the unique identification code described above. The device 1 may be programmed to reject or refuse to process any sample containers 6 that do not include such a feature.

As will also be described in greater detail subsequently with reference to FIGS. 10 and 11, the sample container 6 comprises a central sample chamber 60 within which the clinical sample is initially retained; as well as the plurality of detection chambers 20 which represent the final destination of the various individual sample portions, where the sample portions are illuminated and analysed. A first series of pre-programmed actions that is carried out by the device 1 in Step 125 is therefore to operate the motor 10 to rotate at particular rotational frequencies, in certain predefined directions and for specific durations, in order to re-distribute portions of the clinical sample from the central sample chamber 60 into each of the plurality of detection chambers 20. This series of actions involves the following sequential steps: (a) mixing the clinical sample with a growth medium 62 provided within the sample container 6 to provide a conducive environment for bacterial growth; (b) distributing smaller sample portions into each of a plurality of radially-extending fluidic structures 64 to separate out undesired particles (e.g. sediments etc.) from the sample; (c) mixing the smaller sample portions with a corresponding drug (e.g. an antibiotic) provided within each fluidic structure 64; and (d) retaining the final drug-dosed sample within its corresponding detection chamber 20 for illumination and analysis over time. Of course, in some uses control samples are not exposed to an antibiotic or other drug.

Once this process has been carried out and the various drug-dosed sample portions have been re-distributed into their respective detection chambers 20, the next series of pre-programmed actions taken by the device 1 involves the analysis of the samples in each detection chamber 20. The motor 10 is programmed to drive rotation of the sample carousel 8 and the associated sample container 6 at a constant rotation rate (e.g., 100 or 200 rpm) over a prolonged period of time (e.g., over the course of around 60 to 90 minutes), such that a given point on the sample container 6, e.g. a particular detection chamber 20, carries out a full rotation approx. every 0.6 seconds. Accordingly, in use, at a rotational speed of around 100 rpm or 200 rpm, each detection chamber 20 would pass through the incident beam axis Y at the predetermined interval (e.g. of around every 0.6 seconds for a rotational speed of 100 rpm). Each sample portion in its respective detection chamber 20 is thereby illuminated in turn (every predetermined time interval), and the scattered light is collected by the photodetector 26 and can be processed/analysed at regular intervals over the course of an assay (e.g. a bacterial growth/antibiotic susceptibility assay). Given the frequency of measurements, in some instances, it is envisaged that a (weighted) rolling average of sample measurements may be used to process and combine the scattered light measurements obtained from each detection chamber 20. This would beneficially reduce the noise associated with each averaged sample measurement point (by the square root of the number of individual measurements combined to obtain the weighted average). For example, in some cases, it is envisaged that the rolling average could be applied in relation to 100 measurements (i.e. 60 seconds at the 100 rpm rotational rate envisaged). In some embodiments the rotational speed of the sample carousel 8 (and sample container 6) is selected according to a pre-programmed/factory setting; and may be determined according to the processing speed of the device 1, and/or the frequency of measurements that is desired. Therefore, the rotational speed of the sample container 6 during an assay may be faster or slower than 100 rpm (e.g. between 50 and 300 rpm). Similarly, the length of an assay may also be based on pre-programmed/factory settings, or may in some embodiments be set according to user-preferences. For example, the length of the assay may be determined by the type of bacteria and/or the antibiotics that are to be tested against the bacteria; and may be between about 20 minutes and 4 hours, such as between about 20 minutes and 2 hours, or between about 20 mins and 1.5 hour. In some preferred embodiments, the length of the assay is between about 20 minutes and 1 hour, or between about 30 minutes and 1 hour.

As has been briefly mentioned earlier in this document, the strength of signal generated by the main 'signal' photodiode 26 (in optical arrangements 2 and 2') and 48 (in optical arrangement 2"), as a result of the scattered light intensity measured, is correlated with the amount and/or concentration of (bacterial) particles within the sample being analysed/assayed. In other words, a larger/stronger signal corresponds to a greater amount of light scattering and, hence, a greater scattered light intensity, which in turn indicates a higher concentration of (bacterial) particles within the sample. Graphical representations of the detected signal (based on the scattered light intensity) overtime can thus be used to visualise time-varying changes in bacterial amount and/or concentration in a sample, and thereby illustrate and ultimately determine the susceptibility of the bacteria within that sample to the type and concentration of drug with which that particular sample has been dosed.

Examples of such graphical representations are shown in FIG. 8, where the susceptibility of bacteria in a clinical sample to five different antibiotic drugs was tested. In this example, the sample container 6 was divided into 28 separate detection chambers 20 and associated channels for separating a clinical sample into the 28 detection chambers 20, such that up to 28 separate assays could be performed simultaneously. The 28 assays were divided into four regions—labelled Regions 1 to 4 (see FIG. 8)—and in each region five antibiotic susceptibility tests were carried out alongside one negative control (wherein the detection chamber was altered (e.g., rendered opaque) to prevent incident light from passing through) and one positive control (to follow uninhibited bacterial growth in the absence of any antibiotic). In this instance five different antibiotics were provided, respectively in each of five assay chambers of each region, so that bacterial susceptibility against each antibiotic could be tested in 4 repeats per sample container 6, with one test in each of the four regions. In this way, the reproducibility of the assays around the sample container 6 could also be assessed. The sample container 6 was rotated at around 100 rpm and measurements of scattered light intensity collected from each detection chamber 20 were taken over the course of around 80 minutes.

As is evident from the graphs in FIG. 8, those detection chambers serving as the positive control exhibited generally exponential increase in detected scattered light intensity (and hence a corresponding exponential bacteria amount and/or concentration increase) over the course of the measurement period. This reflects the degree of increase in bacterial amount and/or concentration that would typically be expected (under the assay conditions) if no drugs or other inhibitors were present, and the bacteria were able to grow and replicate normally in a solution containing sufficient growth medium. Meanwhile, those detection chambers serving as the negative control showed minimal detected intensity over the entire measurement period, as would also be expected. Of the five detection chambers containing the various antibiotics, four exhibited changes in detected intensity that indicated a decrease in bacterial amount and/or concentration (relative to the positive control) as a result of the action of the antibiotics—i.e., a curve having a lower or negative gradient relative to the positive control curve, but still (at least initially) having values above the negative control line. Of the various drug-dosed samples, the one which exhibits the greatest decrease in the measured intensity of light scattering over time, compared with the positive control sample, would therefore (in theory) correspond to the sample that has been dosed with the specific type and/or concentration of antibiotic that the bacterial strain present in the sample is most susceptible to. It can therefore be easily determined, over the course of a relatively short period of time, which antibiotic and at which concentration will likely be most effective in treating the patient from which the clinical sample was obtained.

It is of course possible (and in fact quite likely) that multiple different antibiotics may be determined to be ones to which the bacteria in the sample may be susceptible. Various different approaches for determining the most appropriate antibiotic to be used for treatment have therefore been considered. For example, the susceptibility results may be presented to the user in real-time, with the ability to terminate the analysis at any point after at least one antibiotic has been ascertained to be effective. This may however not necessarily be the most appropriate antibiotic to administer; for example, if the response of the bacterial culture changes over a slightly longer time period, or where one antibiotic takes longer initially to take effect. Alternatively, another approach may be to limit the time for the test to be carried out (to e.g., 30 mins, 45 mins or 1 hour) and to present the results to the user after that time: this may mean that multiple antibiotics (or even none) and/or multiple dosage levels may be considered for administration to the patient. Another option is to only present results after a certain number of antibiotics have been deemed effective. This will of course mean that the timescale required for the test will vary. Of course, a combination of these approaches may be adopted.

It will be appreciated that the drugs or antibiotics and the concentrations of each used in each assay may be selected based on a number of determining factors, such as the territory in which the device is to be used and/or on the suspected medical indication and likely bacterial infection to be screened. For example, where a biological sample comprises urine for assaying antibiotic sensitivity of urinary tract infections (UTIs), the antibiotics used may be selected from one or more of the group comprising: Amoxicillin; Amoxicillin/clavulanic acid (2/1); Cefalexin; Ciprofloxacin; Ertapenem; Fosfomycin; Levofloxacin; Mecillinam; Nitrofurantoin; Trimethoprim; Trimethoprim/sulfamethoxazole (1/19). However, the antibiotics selected, and their concentrations or concentration ranges, may take the form of any antibiotic (concentration) designed to provide an anticipated result during the screening.

As is also evident from a comparison of the graphs for the different regions, an increase in the signal noise level was detected during the course of the rotation—the signal measurements obtained for Region 4 (which correspond to detection chambers 20 near the end of each complete revolution) exhibit much greater noise scatter than those obtained for Region 1. The reasons for this increase in noise, along with a technique for handling this increased noise, will be described in greater detail subsequently with reference to FIGS. 11 and 12. The results of this technique are shown in FIG. 13, from which it may be seen that the signal-to-noise ratios across the various detection chambers 20 in the different regions of the sample container 6 show much less variation and are much more consistent with one another. This will be described in greater detail subsequently with reference to FIG. 13.

Nevertheless, it will be appreciated by the skilled person that embodiments of the disclosure described herein provide benefits in relation to parallelisation of sample analysis. Specifically, the design of the sample container 6 means that multiple different drugs (in a variety of different concentrations) can be tested against the same subject's sample in the course of one measurement cycle, and the results directly compared with one another, minimising the equipment and time required to carry out the assessment. Such parallel analysis of the multiple different drugs and concentrations also helps to eliminate environmental effects on the test results from a single subject's sample.

Figure 10:
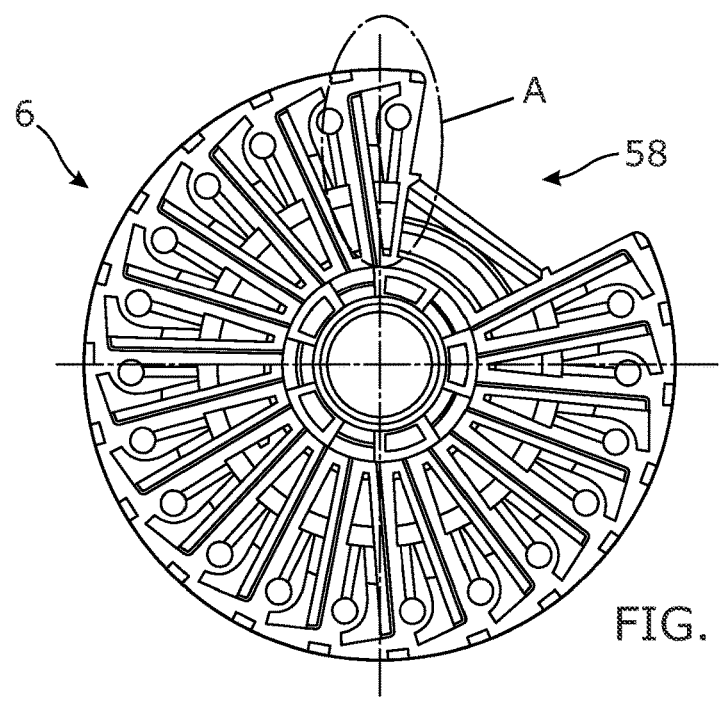
FIG. 10 is a plan view of the sample container of FIG. 9, and FIGS. 10A to E illustrate the different portions of a fluidic structure of the container of FIG. 11.

In order to aid in the understanding of the device's functionality, a brief description of the consumable sample container 6 will now be provided in relation to FIGS. 9 and 10.

As previously mentioned, the sample container 6 is substantially circular in vertical cross-section and comprises a common (central) sample well or reservoir 60 that is in fluid communication with a plurality of detection chambers 20 which are arranged at intervals around a radially outer portion of the container 6. Each detection chamber 20 is fluidly connected to the common sample reservoir 60 via a respective fluidic structure or system 64 (comprising a plurality of fluidic channels 66, 68). However, the detection chambers 20 are otherwise fluidly segregated from each other. The fluidic structures 64, sample reservoir 60 and detection chamber 20 are provided in the base of the sample container 6. The fluidic structures 64 utilise the centrifugal/centripetal forces that are generated via rotation of the sample container 6 by the motor 10 to motivate flow of the sample from the sample reservoir 60, through the respective fluidic channels 66, 68 and finally to the respective associated detection chamber 20. The radial distance of each detection chamber 20 from the central rotational axis X of the sample container 6 corresponds to 'd'—the distance between that rotational axis X of the sample container 6 and the incident beam axis Y—to ensure that as the sample container 6 rotates within the device 1 in use, the light beam from the light source 22 will pass through the detection chambers 20, in turn, to allow individual measurements of scattering intensity to be obtained from each sample portion in the sample container 6.

As will be appreciated, because the detection chambers 20 are provided integrally within the illustrated sample container 6, the sample container 6 (or at least the portion of the sample container 6 comprising the detection chamber 20) is made of a material that is transparent to light (or at least substantially transparent to light at the wavelength of the light source), in order to allow the light from the light source 22 to enter and exit the detection chambers 20. Specifically, in the configurations illustrated, the incident light from the light source 22 passes through the base or underside of the sample container 6, at a position aligned with the detection chamber 20 being illuminated, and exits the top surface of the sample container 6 towards the light collector 24. It will be appreciated, however, that other configurations/relationships between the light source 22, detection chamber 20 and light collector 24 are possible and fall within the scope of the disclosure.

The illustrated sample container shown in FIG. 10 comprises nineteen detection chambers 20 and their associated fluidic structures 64; and has a 'cut-out' segment 58 that is roughly equal in size to four or five detection chambers 20 and their associated fluidic structures 64. However, it will be appreciated that a different number of detection chambers, and/or a differently sized or shaped cut-out segment 58 (or even no cut-out segment, as in the case of the sample container used to generate the data of FIG. 8) could be utilised without departing from the scope of the present disclosure. For reasons of practicality and efficiency in maximising the number of fluidics structures 64, the cut-out 58 may, for example, subtend an angle of between approx. 20° to 60°, suitably between approx. 30° and 50°.

In a convenient mode of manufacture, the fluidics systems 64 are formed as channels, reservoirs and recesses in the lower surface of the sample container 6. Therefore, in order to form a closed system, a base cover 6c having a corresponding surface area footprint to the base of the sample container 6 is attached to the bottom of the sample container 6 to close the assembly and cover off the fluidic systems 64 and sample reservoir 60 that are formed in the lower surface of the sample container 6 (see FIG. 9C). Suitably, the base cover 6c is a film. Without the base cover 6c, the fluidics systems 6 would be open to the environment and would be unable to contain liquid when the fluidic device 1 is in use. This base cover 6c is optically transparent at least in the region axially below (some of) the detection chambers 20, to allow subsequent analysis of the bacteria (or other particulate matter to be assessed for light-scattering ability) in the respective detection chambers 20. In some embodiments the base cover 6c may be opaque to light in particularly defined regions, such as below a detection chamber 20 which is to provide for a negative optical control in use.

The base cover 6c may be attached to the underside of the sample container 6 via any one or more of a few well-known suitable sealing techniques, such as heat sealing, ultrasonic welding, liquid adhesive sealing, or the base cover 6c may comprise a single-sided/double-sided adhesive film. Whichever sealing technique is utilised, it is important to ensure that a high level of optical clarity is maintained and reflection of incident light from the base cover 6c or any adhesive used is minimised (especially in the regions covering the detection chambers 20) to avoid adversely affecting the subsequent analysis process. In addition, the sealing process should be compatible with (and should avoid interference with) any of the components of the sample container 6 (for example, any drugs deposited within the container). In particular, it is desirable that no/minimal adhesive or other chemicals are exposed on the upper surface of the base cover 6c within the fluidics system 64 in order to avoid possible contamination of the liquid sample in use. An additional layer 6d may be attached to the underside of the sample container 6 (see FIG. 9C), and may comprise the previously-described barcode or other means of identification that is configured to be located on the angled portion 58a of the sample container 6.

Conveniently, the sample container 6 comprises a sample receiving well 69 into which a suitable volume of sample is loaded, and contains a growth media or medium 62 (FIGS. 9A, 9B) axially below the receiving well 69 which promotes the growth of bacteria in the sample fluid and that is configured to be mixed with the sample after it has been loaded into the receiving well 69 of the sample container 6 but before the sample enters the common sample reservoir 60 (which is itself located) axially below the growth medium 62. Conveniently, as in the depicted embodiment, the growth medium is dried (e.g. lyophilised or freeze-dried). However, liquid, concentrated growth media may alternatively be used. In alternative embodiments, a powdered, dry growth medium may also be used and may aid in rapid dissolution of the media in a fluid sample. In some embodiments, it is envisaged that the growth media may be contained within a dissolvable capsule/pill.

In one embodiment, the sample container 6 is provided with a cover or cap 6a which can be secured to the container 6 for use. In the depicted embodiment, the cap 6a includes an integral plunger or plug 6b, and one or more projections 65 on the underside of the container plug 6b. As the cap 6a is engaged with the sample container 6, e.g., via a screw-threaded engagement, the or each projection 65 pierces a foil/film 67 covering the growth medium 62, thereby bringing the sample into contact with the growth medium 62. As the cap 6a is screwed further into position to seal the sample within the sample container 6, the plug 69 fills at least a portion of the receiving well 69 and forces the sample and growth medium 62 into the common sample reservoir 60. It will be appreciated that the volume of the receiving well 69 and the extent to which the plug 6b can protrude into the receiving well 69 can be used to regulate the volume of sample and growth medium that is pushed into the common sample reservoir 60. Moreover, the amount/concentration of growth medium contained in the sample container 6 (prior to mixing with sample) may be determined to provide the desired concentration of growth media in the volume of sample/growth medium that is pushed into the common sample reservoir 60. It is noted that should the growth media be contained within a dissolvable capsule or pill, there may be no need for the use of foil/film 67 to cover the growth media; the projections 65 used to pierce this foil/film 67 may therefore also be omitted in such cases if so desired.

Once the sample and the growth medium 62 have been brought into contact with one another and the cap 6a secured, the sample container 6 can be inserted into the appropriate location in device 1. Preferably, as previously discussed, the sample container 6 is designed to be inserted into the device 1 in a particular orientation. Beneficially, an asymmetry in the sample container 6—in the depicted embodiments, specifically the cut-out segment 58 of the sample container 6, can be used to align the sample container 6 with the main optical support structure 28 initially. In this orientation, the sample container 6 does not, therefore, extend substantially through the cut-out 30 of the optical support structure 28 when the sample container 6 is initially inserted into the device 1. In other words, the relative alignment of the cut-out segment 58 with the optical support structure 28 guides the insertion of the sample container 6 into the device 1, and avoids the potential for damage to the device 1 and/or the sample container 6 as a result of incorrect alignment during insertion.

Once the sample container 6 has been inserted into the device 1, a programmed set of actions commences. The effects of these actions on the fluid sample within the sample container 6 will now be described with reference to FIG. 10.

Figures 10A, 10B, 10C:
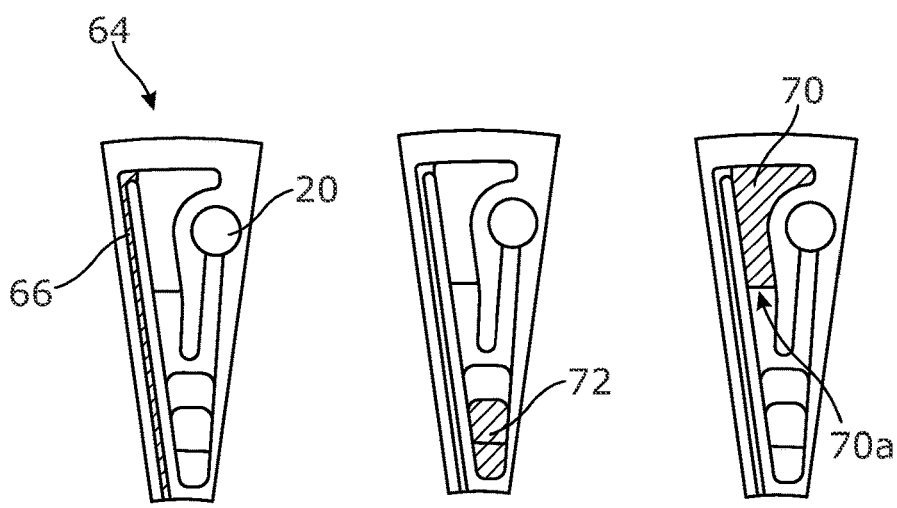
Figures 10D, 10E:
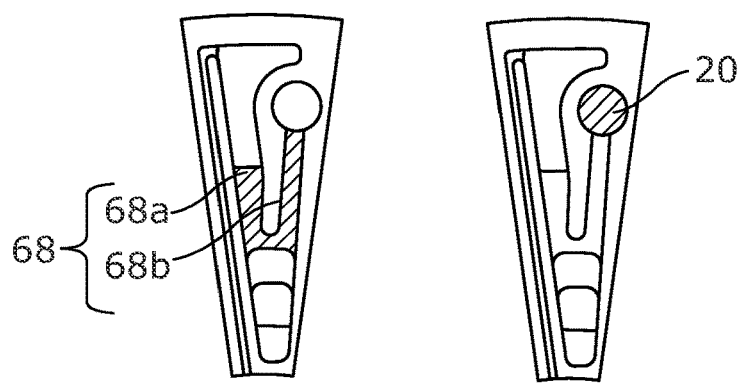

As shown in FIG. 10A, each fluidic structure 64 and its associated detection chamber 20 constitute a substantially self-contained system within the sample container 6 (indicated by the circled 'A' in FIG. 10). Despite the presence of a common sample reservoir 60, due to the action of centripetal/centrifugal forces in use, fluid flow between adjacent fluidic structures 64 is not possible, thereby avoiding possible cross-contamination between the various drug-dosed sample portions which are to be individually analysed in their respective detection chambers 20. Each fluidic structure 64 comprises a first radially extending 'entry' microchannel 66 (highlighted in FIG. 10A) which is in fluid communication, at its radially outermost extent, with a clarification (sedimentation) chamber or well 70—highlighted in FIG. 10C. The clarification chamber 70 is in fluid communication, at its radially innermost extent and via a weir 70a (FIG. 10B), with a second generally U-shaped microchannel 68—highlighted in FIG. 10D. This second microchannel 68 has a pair of radially extending first and second channel arms 68a, 68b, that are configured to enable fluid flow along roughly antiparallel directions. The first channel arm 68a extends between the clarification chamber 70 and an 'air spring' or pneumatic (by-pass) valve 72 (sometimes also known in the art as a 'pneumatic spring' or 'air ballast chamber')—highlighted in FIG. 10B; while the second channel arm 68b extends between the air spring 72 and the detection chamber 20. The detection chamber 20 is highlighted in FIG. 10E. Suitably, in any embodiments of the disclosure, each of the fluidic channels 66, 68a and 68b are arranged approximately radially.

In this instance, the term "air spring" is used to refer to a pocket of gas which is compressed and put under increased pressure as fluid (liquid) moves through the fluidic channels of the fluidic structure 64, and can thus be configured to prevent fluid flow between the two channel arms 68a, 68b unless a sufficient fluid force is applied to the gas. In other words, an air spring provides a fluid sealing and entry control functionality between different regions of a fluidic structure 64, such as between two channel arms 68a, 68b. Considered in another way, the movement of sample fluid with respect to the air spring 72 may be controlled by the balance/difference between pressures: i.e. the centrifugal pressure difference caused by the rotating disc of the sample container 6 must overcome the increased pressure (overpressure) caused by the reduced gas volume before liquid will move past the air spring valve mechanism 72. It will however be appreciated that alternative valve mechanisms or sealing mechanisms could be used instead to provide corresponding functionality without departing from the scope of the present disclosure.

To begin with, the motor 10 rotates the sample container 6 alternately clockwise and anticlockwise (i.e. executing reciprocal/oscillatory motion) at an initial relatively low speed (for example, around or below 500 rpm) and for a pre-defined period of time (between around 30 s to around a few minute) to ensure thorough mixing of the sample with the growth medium 62 within the sample reservoir 60.

Subsequently, the sample container 6 is rotated in one direction at an increased rotational speed; the speed used varies depending on various factors such as the geometry of the sample container 6, therefore in some cases speeds of up to between about 1,600 and 1,900 rpm may be utilised, whereas in other cases speeds of up to around 2600 rpm may be utilised where greater centrifugal forces are desirable. This generates sufficient centrifugal force to cause the mixed sample to flow outwards from the central sample reservoir 60 along each of the radially extending first fluidic channels 66 and into the respective clarification chambers 70. This rotation speed is maintained for a pre-defined period (for example, around 30 seconds) to allow the sample to substantially fill each of the respective clarification chambers 70 and to apply sufficient centrifugal forces to cause heavy particles (e.g., of about 10 μm or more) to sediment around the outer edge of the clarification chambers 70. Towards the end of this spin cycle, enough sample fluid has entered the clarification chamber 70 to raise the fluid level in those chambers above that of the weir 70a; the overflowing fluid is displaced into the first channel arm 68a of the second fluidic channel 68. Any sediments that are present in the sample fluid are deposited in and remain within the clarification chambers 70, such that the fluid sample entering the fluidic channel 68 contains essentially only particles of below about a few microns, such as bacterial cells. Indeed, centrifugal force acting on the liquid sample, in use, pushes heavier particles/unwanted impurities outwards to the most radially outer wall of the clarification chambers 70, such that these impurities are held in a position that is furthest from the weir 70a.

Once most of the fluid sample has been redistributed from the central sample reservoir 60 into the individual fluidic structures 64, the rotation speed of the sample container 6 is increased (the speed used varies dependent on various factors including the geometry of the sample container 6, therefore in some cases speeds of e.g., above 1,900 rpm or above 2,600 rpm and up to around 3,000 rpm, 3,600 rpm or 4,000 rpm). This provides sufficient centrifugal force for the sample fluid flow to overcome the pressure exerted by the air spring 72, and to enter the second channel arm 68b of the second fluidic channel 68. Once the air spring 72 'seal' (pressure block) has been overcome in this manner, the sample fluid is able to flow through the second microchannel arm 68b and to enter the detection chamber 20. This process of directing the sample fluid from the clarification chamber 70 to the detection chamber 20 may take, for example, up to around 20 seconds or so, so as to ensure that adequate sample fluid enters each detection chamber 20 whilst avoiding the potential for antibiotic contamination of the main fluid reservoir 60 (explained in more detail below).

In the illustrated embodiment, a particular type and concentration of drug (antibiotic) is present in each detection chamber 20. Conveniently, the drug/antibiotic is in dried form, e.g., as a result of having been initially deposited on the base of the detection chamber 20 during manufacture of the sample container 6 and dried thereon. As the skilled person will appreciate, however, other forms of drug/antibiotic may be used according to preference or suitability—for example, the drug may be deposited onto a paper (e.g., a filter paper), which is placed in a region of the fluidic structure 64 to be dissolved into the liquid sample, or the drug may be present in liquid form. Suitably, as the sample fluid flows into and fills the detection chamber 20, it therefore mixes with the deposited drug to the desired concentration. Once sufficient sample fluid has entered the detection chamber 20, the rotation speed of the sample container 6 is preferably reduced (e.g., from around 4,000 rpm, 3,600 rpm or 3,000 rpm to around 1,500 rpm) to retain the fluid sample within the detection chamber 20. By way of explanation, by reducing the rotational speed, the air in the air spring 72 is free to expand once more as there is less of a pressure force on it. When this happens, the fluid in clarification chamber 70 is pushed back up the first fluidic channel 66 into the central sample reservoir 60. This creates an air barrier between the fluid in the detection chamber 20 so no cross contamination can occur. Moreover, any backflow of fluid from the detection chamber 20 is prevented because once the detection chamber 20 is evacuated of gas, then can be no force pushing the liquid sample radially inwards towards the air spring 72. Inertial mixing of the sample fluid to solvate its respective drug is then effected via reciprocal rotation of the sample container 6 (i.e. alternating clockwise and anticlockwise rotations) at a relatively low speed (e.g. between around 1,300 rpm and 1,800 rpm) for a pre-defined period of time (around a few minutes, e.g. 3 minutes).

The initial sample distribution phase is now complete, and the illumination, measurement and analysis of the samples in their individual detection chambers 20 can commence. During this process, the motor 10 is configured to rotate the sample container 6 at a relatively low speed—e.g., of around only 100 rpm or 200 rpm. As this process was described in detail earlier, it will not be repeated here.

Figure 11:
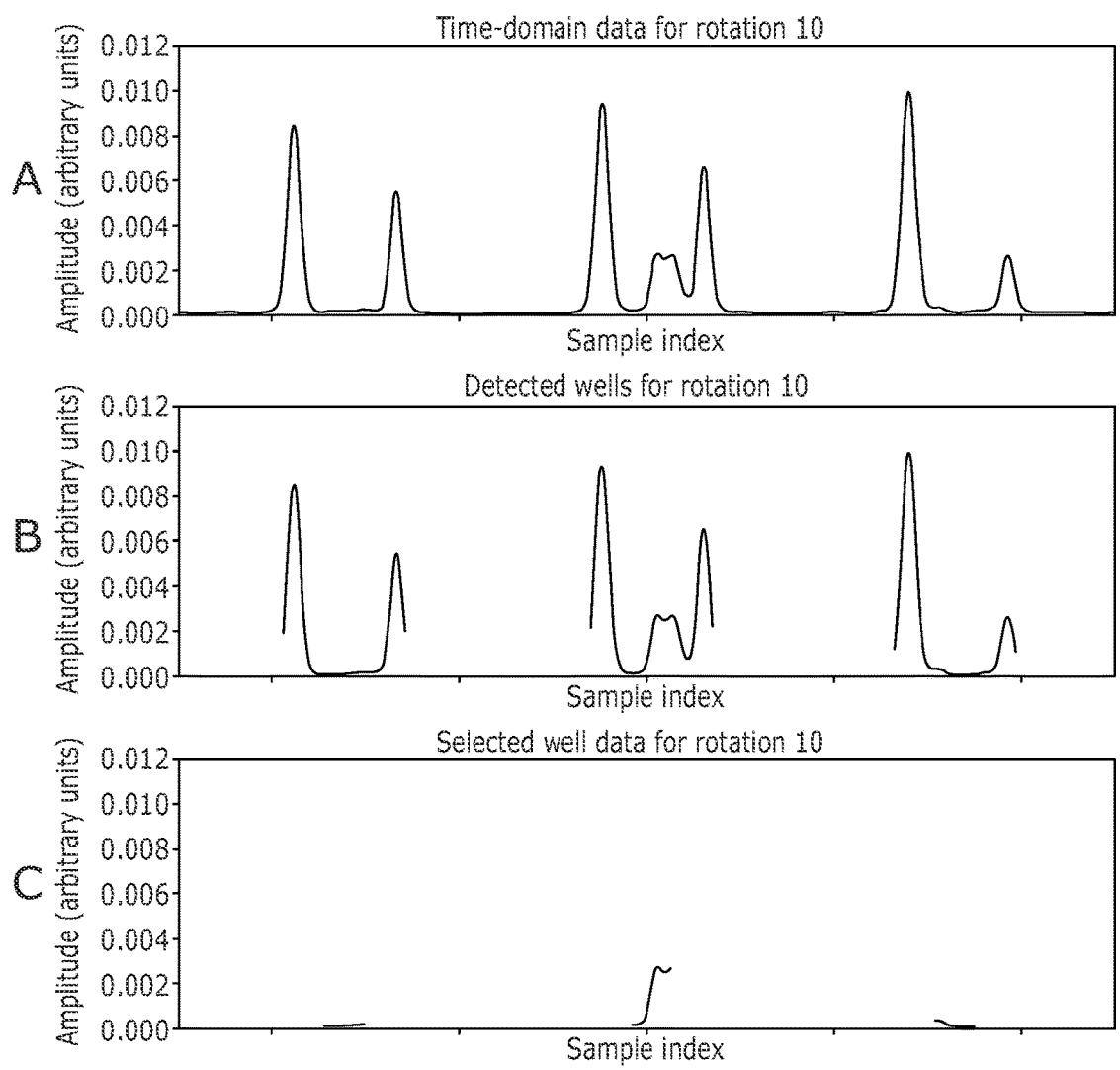
FIG. 11 show plots of detected intensity measured as a function of time when the sample container of FIG. 10 is used in the device of FIG. 1.

Some additional details regarding aspects of the processing used to extract the wanted signal—i.e., the portion of the measured signal corresponding to the light scattered by the bacteria particles in the sample—will now be provided with reference to FIG. 11. This figure shows three plots of detected signal intensity over time, illustrating a well-windowing technique used to extract the appropriate portions of the signal for analysis.

The inventors have noted that there are periodic peak features occurring within the detected signal intensity measured by the photodetector, which have been found to occur at the points where the light from the light source is incident on the walls/edges of the detection chambers 20, and determined to be due to increased scattering of the incident light by the internal walls of the detection chamber 20, rather than by the particles within the sample. FIG. 11 thus shows how these peak features can be used during signal/data processing to more accurately pinpoint those segments of the measured intensity signal that correspond to the light passing through and being scattered by the sample in the detection chamber 20. FIG. 11A (upper graph panel) depicts the measured scattered light intensity at the photodetector 26 as the sample container 6 rotates relative to the light source. The scattered light trace depicted spans three detection chambers 20, i.e., three openings 18 in the sample carousel 8 and the solid regions on either side thereof. Removal of the detected light intensity between collection chambers 20/openings 18 leaves just the detected scattered light intensity trace for the region spanned by the three detection chambers 20, as shown in the middle graph panel (FIG. 11B). The processor may be configured to identify such periodically occurring peak features in the measured light intensity (as shown in FIGS. 11A and 11B), which are not due to particles in the sample, to extract the segments of measured intensity between adjacent peak features from the rest of the signal (as shown in FIG. 11C, lower graph panel), such that the measuring and determining of scattered light intensity only in relation to the extracted segments (corresponding to light scatter by the sample and not by the edges of the detection chambers 20) can be performed to assay bacterial growth. This may advantageously avoid performing processing on the portion of the signal containing large noise spikes, and may allow the signal to be amplified as appropriate.

This technique provides an improvement in noise reduction relative to a (relatively more straightforward) method of simply using a pre-defined 'time window' to extract the 'wanted' signal obtained measurements, namely extracting the data for each sample within a pre-defined time period or 'window' at a given timing offset from the start of each new revolution of the sample container 6. This is because small variations in motor speed result in misalignment of the pre-defined 'time window' with the actual signal corresponding to light scattered from the bacteria in the sample—i.e., the pre-defined 'time window' will 'drift' over time relative to the actual wanted signal. This in turn means that the 'time window' for data extraction will overlap with the peak features (discussed above, resulting from scattering by the edges of the detection chambers 20), and the extracted signal will include a greater amount of this increased scatter from the edges of the detection chambers 20, therefore exhibiting greater noise levels. Such 'drift' or misalignment between the extraction 'time window' and the actual time period within which the wanted signal lies will be more pronounced in those samples that are measured towards the end of a revolution, as is evidenced by the increased noise in the graphs of Region 4 (shown in FIG. 8). It is noted however that the well-windowing technique described above may potentially be more easily implemented in the context of post-processing of the sample measurements, rather than as a mechanism for extracting specific signal segments in real-time for processing. An additional or alternative mechanism for reducing the noise in the extracted signals has also been developed, which enables more accurate identification of the 'window' within which the wanted signal from each detection chamber 20 lies; this mechanism will now be described in more detail in relation to FIGS. 12A and 12B.

Figure 12A:
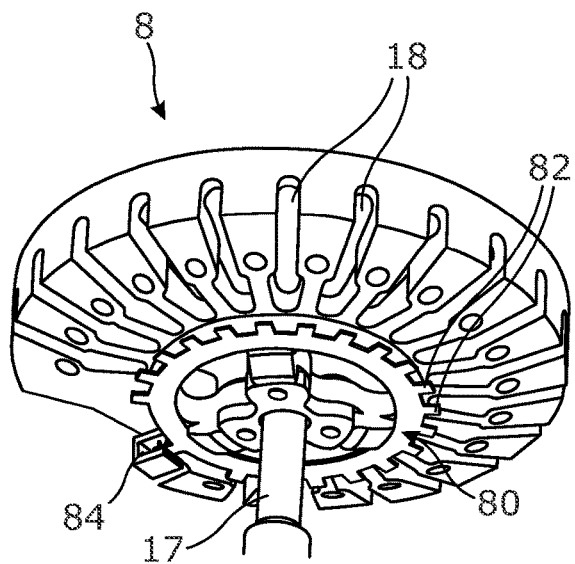
FIG. 12A is a bottom perspective diagram of a sample carousel that may be used in the device of FIG. 1 that interfaces with the sample container of FIG. 9.
Figure 12B:
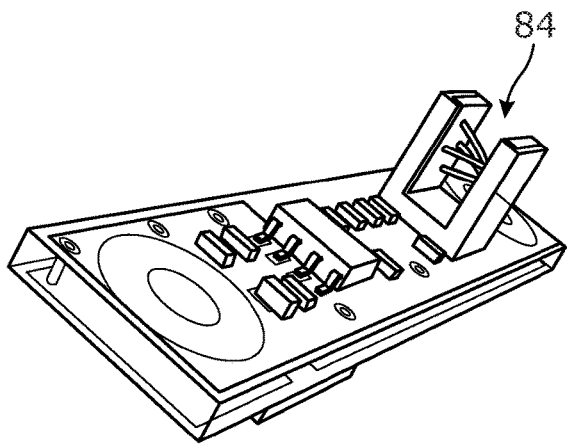
FIG. 12B is a perspective diagram of the controller that is used in the sample carousel of FIG. 12A.
Figure 13:
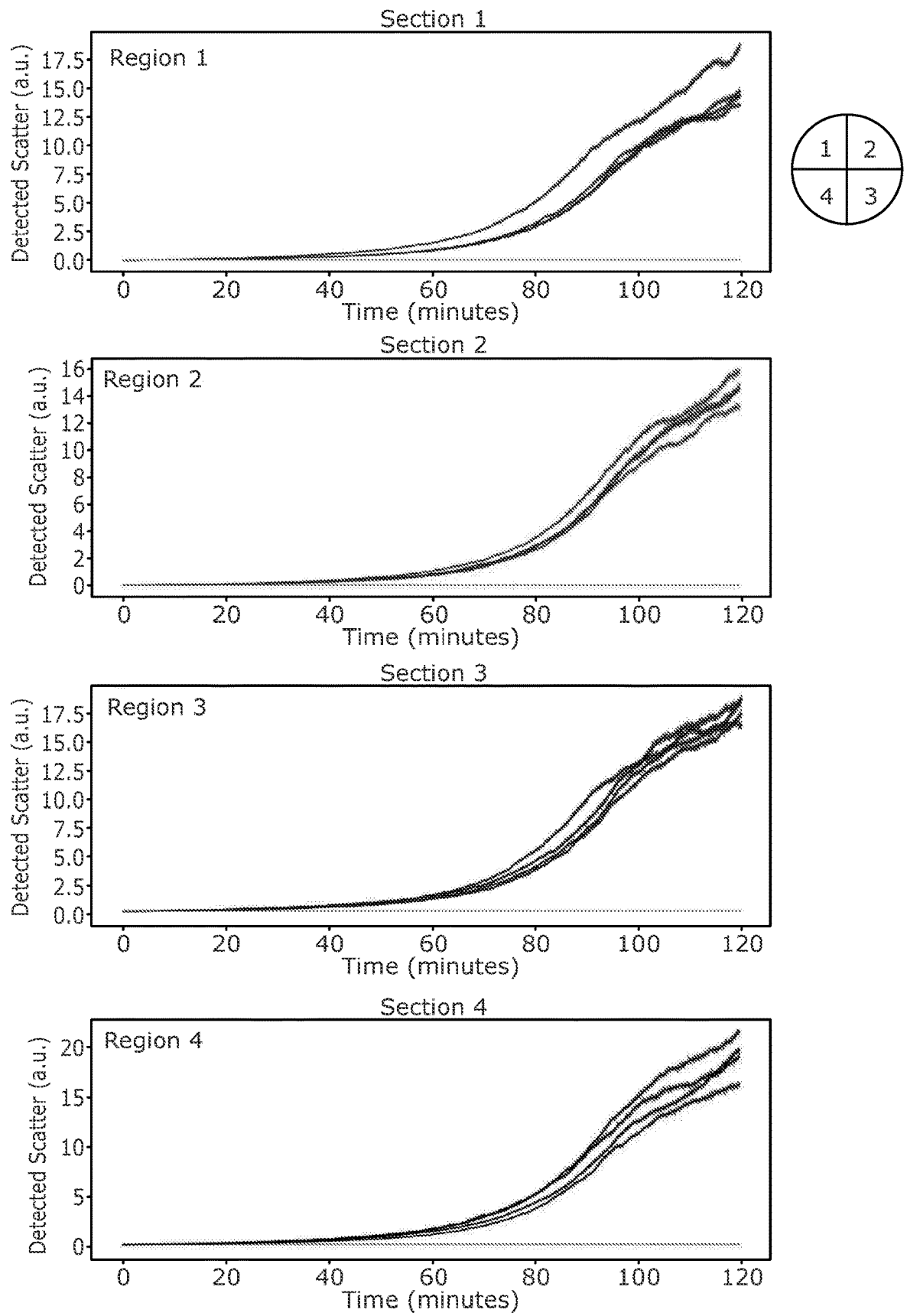
FIG. 13 shows different plots of detector intensity output as a function of time in the device of FIG. 1, illustrating the signal-to-noise ratio obtainable in the device of FIG. 1.

FIG. 12A provides a bottom perspective view of the sample carousel 8, with reference to which further details of a calibration aspect of the intensity measurement process will now be described. FIG. 12B provides a close-up view of a controller used during this calibration in combination with the sample carousel 8.

In the depicted embodiment of FIG. 12A, the sample carousel 8 comprises an additional calibration ring or toothed wheel 80 located on its underside and comprising a plurality of calibration features or teeth 82. In the illustrated embodiment, the calibration features 82 correspond to a plurality of radially extending spokes protruding from the calibration ring 80 at intervals, and arranged such that each calibration feature 82 is associated with a corresponding one of the plurality of openings 18.

In use, when the sample container 6 is engaged with the sample carousel 8, each calibration feature 82 will therefore also be associated with a corresponding one of the plurality of detection chambers 20 in the sample container 6. The device 1 further comprises a calibration reader or optical encoder 84 arranged within the device 1 so as to be located adjacent to the underside of the sample carousel 8, and configured to interface with each of the calibration features 82 in turn as the sample carousel 8 is rotated by the driving shaft 17 in use. Specifically, the calibration reader 84 comprises an optical arrangement that is configured to detect each calibration feature 82 passing through it, for example via detection of a decrease or loss in optical signal that is caused by the calibration feature 82 passing through and temporarily breaking an optical beam path within the calibration reader 84 (as shown in FIG. 12B in more detail).

As the calibration features 82 are each associated with one of the detection chambers 20, the calibration reader 84 can be used to detect each calibration feature 82 associated with each opening 18 of the sample carousel 8, and send a signal to a controller/processor of the device 1 to commence measurement of scattered light intensity a predetermined time period after detection of the calibration feature 82, and for a predefined period of time sufficient to encompass the period wherein the detection chamber 20 intercepts the light from the light source 22 without impinging on the walls of the detection chamber 20 (i.e. for an interval sufficient to obtain the readings exemplified in FIG. 11C). Beneficially, in this way, the light scatter measurement window is reset multiple times per revolution of the sample container 6 to ensure that the photodetector readings are appropriately in phase with the detection chambers 20. It will be appreciated that the number of calibration features can be selected according to preferences: for example, there may be a calibration feature associated with every opening 18 in the sample carousel 8, or there may be one calibration feature associated with a predetermined group of openings 18 (e.g., one calibration feature 82 for every 2, 3, 4, 5 or 6 etc. openings 18).

Alternatively, the calibration features 82' may take a different form. For example, as is shown in the depicted embodiment of FIGS. 2, 3A and 3B, the calibration features 82' take the form of ribs, fins or flags that are provided at intervals around the circumference of the sample carousel 8, and (as shown in those figures) extend substantially downwardly from the base of the sample carousel 8. These ribs 82' may therefore be moulded and form an integral part of the sample carousel 8. In this instance, the calibration reader 84 may instead be installed and oriented such that the vertically-extending ribs 82' pass through the optical arrangement of the calibration reader 84. In the depicted embodiment of FIGS. 3A and 3B, one calibration feature 82' is associated with each opening 18 of the sample carousel 8 such that the passage of each calibration feature 82' through the optical arrangement of the calibration reader 84 may form a trigger for a reading or measurement of scattered light to be obtained from each corresponding detection chamber 20. Beneficially, this helps to prevent the drift that occurs in the 'window' due to variation in motor speeds, as a specific indicator is associated with each opening 18 and hence with each detection chamber 20.

FIG. 13 shows plots of detector intensity output as a function of time in the device of FIG. 1, illustrating the signal-to-noise ratio obtainable when utilising the calibration features 82, 82' and calibration reader 84. As was the case for FIG. 8, the device 1 was divided into four regions or quadrants, and each of the four plots represents the detector intensity measurements obtained from the detection chambers 20 located within the corresponding region. It is noted that no antibiotics or other drugs were provided in the device when producing the detector intensity output plots of FIG. 13, and therefore (as would be expected) these plots do not show any significant decrease in detector intensity output that might be expected if the bacteria present in the sample were demonstrating susceptibility to the antibiotics (as is the case in the plots of FIG. 8). However, what is evident from the plots of FIG. 13, is the significant reduction in variance of signal-to-noise that is observed in all cases: the plotted detector intensity is relatively consistent across all four regions, with no single region demonstrating increased noise over any of the other regions (as was the case for Region 4 in FIG. 8).

In some cases, it is envisaged that the calibration reader 84 (or a processor associated with the photodetector 26) may be configured to calculate the time interval between adjacent calibration features 82 passing through the reader 84, and to compare those calculated intervals with the pre-determined intervals at which the intensity of collected scattered light is being measured. If there is a discrepancy between the measured 'calibration' time intervals and the pre-determined measurement time intervals and that discrepancy exceeds a predetermined time interval, the processor may then be configured to alter the measurement time intervals to align them with the 'calibration' time intervals. This ensures that the intensity measurements are being taken when the detection chambers 20 are accurately aligned with the incident beam axis—i.e., when the light from the light source is incident substantially through the centre of the detection chamber 20.

Many modifications may be made to the above examples without departing from the scope of the present disclosure as defined in the accompanying claims.

For example, the drugs need not be provided within the detection chambers 20 but could instead be located at a different portion of the fluidic structure 64, for example within the second channel arm 68b of the second microchannel 68. Additionally or alternatively a second pneumatic valve or air spring may be provided at a position in the flow path after the detection chamber, so as to enable a different mechanism for effective mixing of the sample with the drug (via a 'sloshing' action back and forth between the pair of air springs).

Furthermore, it is noted that the design of the sample container 6 may be altered to vary the optical path length of light passing through the detection chamber 20 by varying the depth of the detection chamber well. Increasing the optical path length will increase the signal: the light will pass through more sample and interact with more bacteria particles in the process. Example path lengths that may be considered are between 4 and 10 mm (e.g., well depths of 4, 6, 8 or 10 mm); altering the optical path length will also involve altering the sizes of the other features in the fluidic system 64, such as the clarification chamber 70 and the air spring 72.

Other mechanisms for improving the signal to noise ratio involve 'masking' of the edges of the detection chambers 20, for example by securing a thin film or sheet of plastic or other thin material to the base of the sample container 6 to prevent light from entering or interacting with other portions of the sample container 6—for example, the openings 18 in the sample carousel 8 may be smaller in diameter than the diameter of the detection chambers 20.

Additionally, detection sensitivity can be increased by making some slight (optional) alterations to the optical arrangement 2 to increase the signal-to-noise ratio of the detected scattered light. For example, the second photodetector 48 which collects the non-scattered light may be tilted or angled relative to the path of the non-scattered light beam to reduce unwanted reflection of this non-scattered light back into the optical system (where it may interact with the other light beams). In some instances, the first photodetector 26 may be screened to reduce unwanted detection of stray light within the optical system.

As will be appreciated, minimising the number of (separately) machined parts of the optical assembly can increase the precision of the light beam output from the light source 22 and the alignment of this light beam with the detection chambers 20 and the aperture 46 in the light collector 24 when the optical assembly is assembled. In addition, in some instances and particularly where the light source takes the form of a laser (diode), the laser may be contained in a machined/easily replicated laser block to increase the consistency of the laser beam position (and hence increase the ease with which good alignment within the optical system can be maintained) when carrying out measurements.

In relation to maintaining a consistent alignment of light beam through the optical system, an additional sensor (such as an accelerometer) can be incorporated within the device 1 to measure the vibrations occurring within the device 1 (e.g., as a result of the motor 10 rotating the sample container 6 and/or the fans 42 in the temperature control module 14). This can help to ensure that any vibrations are maintained within/below an acceptable range so as to avoid adversely affecting the alignment of the components in the optical arrangement 2.

Figure 14:
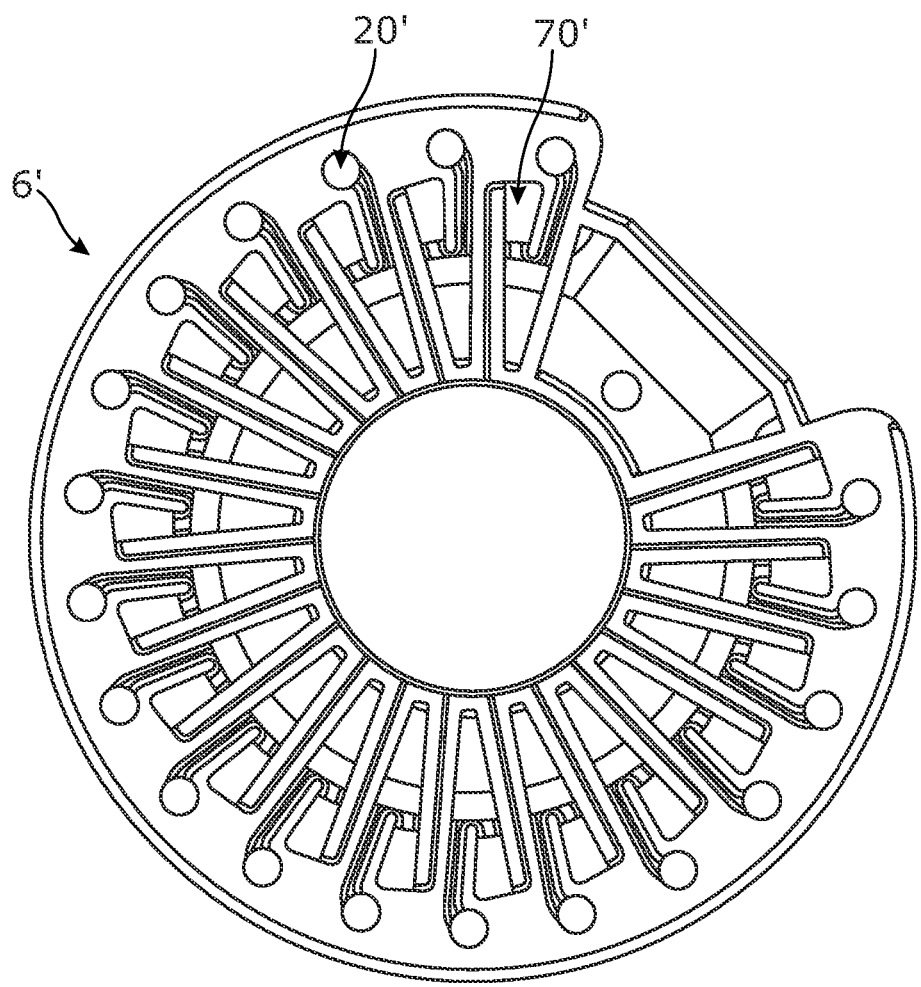
FIG. 14 is a plan view of an alternative design of a sample container that can also be used in the device of FIG. 1 to analyse clinical samples.

Finally, an alternative design of the sample container 6' has also been envisaged which is illustrated in FIG. 14. It can be seen from this figure that the relative locations of the clarification chamber 70' and detection chamber 20' in this alternative sample container 6' differ from the relative locations of the clarification chamber 70 and detection chamber 20 in the sample container 6 that was shown in FIG. 10. Specifically, in the sample container 6 of FIG. 10, the radially outermost extent of the clarification chamber 70 is located at a greater distance from the central rotational axis of the sample container 6 compared with the radially outermost extent of the detection chamber 20. However, in the alternative sample container 6', an opposite configuration is utilised: the radially outermost extent of the detection chamber 20 is located at a greater distance from the central rotational axis of the sample container 6' than the radially outermost extent of the clarification chamber 70'. This latter arrangement illustrated in FIG. 14 advantageously increases the ease with which the fluid sample can be retained within the detection chamber 20' for illumination and measurement, since the centrifugal forces acting upon the fluid tend to cause the fluid to move towards the radially outermost extent of the fluidics system 64. It will be appreciated that such adjustments of the relative location of the detection chamber 20 may necessitate some consequential changes to the relative locations of the components of the optical arrangement 2 to maintain the alignment of the light source 22, detection chamber 20, light collector aperture 46 and photodetectors 26, 48.

What is claimed is:

1. A device comprising an optical apparatus for monitoring bacterial growth of a drug-dosed liquid biological sample, the device comprising:
   a sample container port for receiving a sample container, in use, the sample container having at least one detection chamber for containing the drug-dosed sample; and
   the optical apparatus comprising:
      a light source configured to emit light along an incident beam axis that, in use, intersects with at least one detection chamber of the sample container, and to illuminate the drug-dosed sample contained within the detection chamber;
      a first photodetector configured to receive light scattered by bacteria in the sample;
      a light collection arrangement configured to:
         collect light exiting the detection chamber that has been scattered in a forward direction by bacteria in the sample, in a range of scattering angles between about +/−4 and +/−20 degrees relative to the incident beam axis, and to direct the collected scattered light to the first photodetector; and
         prevent non-scattered light travelling parallel to the incident beam axis and exiting the detection chamber from reaching the first photodetector; and
      at least one processor configured to:
         (a) measure an intensity of the scattered light received by the first photodetector;
         (b) determine a corresponding representative amount or concentration of bacteria present in the sample based on the intensity of the scattered light;
         (c) repeat the measuring step (a) and the determining step (b) at a series of pre-determined intervals to determine changes in the representative amount or concentration of bacteria present in the sample as a function of time; and
         (d) determine a corresponding susceptibility of the bacteria in the sample to the respective drug.

2. The device of claim 1, wherein:
   only light collected in the angular range between about +/−4 and +/−20 degrees relative to the incident beam axis is directed to and received by the first photodetector; or
   the range of scattering angles of collected scattered light is between +4 and +16 degrees and −4 and −16 degrees relative to the incident beam axis.

3. The device of claim 1, wherein the light collection arrangement comprises:
   (i) a concave elliptical reflector configured to collect and reflect only light in the angular range between about +/−4 and +/−20 degrees relative to the incident beam axis towards the first photodetector so that it is received by the first photodetector;
(ii) a concave elliptical reflector configured to collect and reflect forward-scattered light in the angular range between about +/−4 and +/−20 degrees relative to the incident beam axis towards a condenser, the condenser arranged to receive light reflected by the concave elliptical reflector and to focus the received light onto the first photodetector; or
iii) a concave elliptical reflector shaped to reflect the forward-scattered light from the sample to the first photodetector or a condenser, and wherein the concave elliptical reflector comprises an aperture aligned with the incident beam axis and configured to allow non-scattered light from the detection chamber to pass through the concave elliptical reflector.

4. The device of claim 1, wherein the optical apparatus further comprises a second photodetector arranged to receive non-scattered light.

5. The device of claim 1, comprising a sample container carousel arranged inside the sample container port for engaging a sample container comprising one or a plurality of detection chambers and wherein the sample container carousel is configured to bring a detection chamber containing at least a portion of the biological sample in the sample container into alignment with the incident beam axis of the light source of the optical apparatus.

6. The device of claim 5, which comprises a motor operably coupled to the sample container carousel and configured to rotate the carousel to periodically bring a detection chamber containing at least a portion of the biological sample into and out of alignment with the incident beam axis of the light source.

7. The device of claim 5, wherein the sample container carousel comprises one or more openings configured to align with the one or plurality of detection chambers of the sample container when the sample container is correctly engaged with the sample container carousel in use.

8. The device of claim 5, wherein the sample container carousel includes one or more detectable calibration features for determining the position and/or orientation of the sample container carousel relative to the incident beam axis of the light source.

9. The device of claim 8, which comprises a calibration feature reader communicating with a processor of the device, in use, for determining a time interval between detection of a calibration feature by the calibration feature reader and an associated detection chamber coming into alignment with the incident beam axis of the light source.

10. The device of claim 9, wherein a processor of the optical apparatus:
(i) communicates with the first photodetector to measure the intensity of the scattered light received by the first photodetector during a predetermined time window corresponding to the time period during which a detection chamber of the sample container is in alignment with the incident beam axis of the light source;
(ii) adjusts the length of the pre-determined intervals based on the detection of the or each calibration feature; or
(iii) is programmed to repeat the steps of measuring an intensity of the scattered light received by the first photodetector and determining a corresponding representative amount or concentration of bacteria present in the sample as a function of time periodically over a time period of: between about 20 minutes and about 2 hours, between about 20 minutes and about 1.5 hours, between about 20 minutes and about 1 hour or between about 30 minutes and about 1 hour.

11. The device of claim 1, further comprising a temperature control system for controlling the temperature of air inside the device.

12. The device of claim 11, comprising at least one heating element arranged, in use, to bring warm air into contact with a sample container received inside the sample container port of the device, so as to maintain a biological sample within a detection chamber at a desired temperature.

13. The device of claim 11, comprising a pair of heating elements, each heating element operably associated with a fan to push warmed air towards the sample container port, in use to heat a sample within a detection chamber of a sample container received within the sample container port of the device.

14. The device of claim 1, wherein the processor of the optical apparatus is configured to identify a plurality of periodically occurring peak features in the measured light intensity, and to carry out the measuring step (a) and the determining step (b) only between adjacent peak features.

15. A system for monitoring bacterial growth of a drug-dosed liquid biological sample, the system comprising:
a device comprising:
a sample container port for receiving a sample container, in use, the sample container having at least one detection chamber for containing the drug-dosed sample; and
an optical apparatus comprising:
a light source configured to emit light along an incident beam axis that, in use, intersects with at least one detection chamber of the sample container, and to illuminate the drug-dosed sample contained within the detection chamber;
a first photodetector configured to receive light scattered by bacteria in the sample;
a light collection arrangement configured to:
collect light exiting the detection chamber that has been scattered in a forward direction by bacteria in the sample, in a range of scattering angles between about +/−4 and +/−20 degrees relative to the incident beam axis, and to direct the collected scattered light to the first photodetector; and
prevent non-scattered light travelling parallel to the incident beam axis and exiting the detection chamber from reaching the first photodetector; and
at least one processor configured to:
(a) measure an intensity of the scattered light received by the first photodetector;
(b) determine a corresponding representative amount or concentration of bacteria present in the sample based on the intensity of the scattered light;
(c) repeat the measuring step (a) and determining step (b) at a series of pre-determined intervals to determine changes in the representative amount or concentration of bacteria present in the sample as a function of time; and
(d) determine a corresponding susceptibility of the bacteria in the sample to the respective drug;
a sample container comprising a plurality of detection chambers, each detection chamber configured to contain a drug-dosed liquid biological sample;
wherein the system further comprises:
a sample positioning mechanism configured to align each of the plurality of detection chambers in turn with the incident beam axis such that the light source illuminates the drug-dosed liquid biological sample contained within the illuminated detection chamber.

16. The system of claim 15 wherein the sample positioning mechanism comprises a rotation or carousel mechanism configured to rotate the sample container, so as to sequentially align each of the plurality of detection chambers with the incident beam axis.

17. The system of claim 15, further comprising a support structure arranged to support the optical apparatus, wherein the support structure comprises an opening configured to receive a portion of the sample container comprising at least one of the plurality of detection chambers, such that when the portion of the sample container is located within the opening, at least one of the plurality of detection chambers is locatable along the incident beam axis between the light source and the light collection arrangement.

18. A method for determining susceptibility of bacteria in a sample to a drug, the method comprising:
(a) containing a drug-dosed liquid biological sample in a detection chamber of a sample container;
(b) illuminating, by a light source, the sample in the detection chamber with light emitted along an incident beam axis that passes through the detection chamber;
(c) collecting, by a light collector, light scattered by interaction with bacteria in the sample, the light being scattered in a forward direction in a range of scattering angles between +/−4 and +/−20 degrees relative to the incident beam axis;
(d) concentrating, by the light collector, the collected scattered light onto a first photodetector;
(e) determining, by a processor an intensity of scattered light collected by the first photodetector, and a corresponding representative amount or concentration of bacteria present in the sample;
(f) repeating, by the processor, the determining step at a series of pre-determined intervals;
(g) determining, by the processor, changes in the representative amount or concentration of bacteria in the sample as a function of time; and
(h) determining, by the processor, susceptibility of the bacteria in the sample to the drug used to dose the sample based on the determined changes in the representative amount or concentration of bacteria in the sample as a function of time.

19. The method of claim 18, wherein the sample container comprises a plurality of detection chambers, at least two of the plurality of detection chambers containing (i) a sample dosed with a different drug or (ii) a sample dosed with the same drug at different concentrations of the drug, and the method comprises:
sequentially locating each of the plurality of detection chambers containing the drug-dosed sample in the light emitted along an incident beam axis;
carrying out each subsequent step of the method in respect of each of the plurality of detection chambers; and
determining the relative susceptibility of the bacteria in the samples to (i) the respective drugs or (ii) to the respective concentrations of the drug used to dose the samples to identify the most effective drug for use in a therapeutic treatment regime.

20. The method of claim 18, comprising:
collecting, by a second photodetector, non-scattered light passing through the or each detection chamber parallel to the incident beam axis; and
comparing an intensity of the non-scattered light collected by the second photodetector with an intensity of the scattered light collected by the first photodetector in respect of the same detection chamber.

21. The device of claim 4, wherein the second photodetector is positioned on the opposite side of the light collection arrangement to the sample, and aligned with the incident beam axis to receive the non-scattered light.

22. The device of claim 12, further comprising at least one air flow regulator arranged, in use, to bring warm air into contact with a sample container received inside the sample container port of the device, so as to maintain a biological sample within a detection chamber at a desired temperature.

* * * * *